US005167824A

United States Patent [19]

Cohen et al.

[11] Patent Number: 5,167,824

[45] Date of Patent: Dec. 1, 1992

[54] SEPARATION BY CARRIER MEDIATED TRANSPORT

[75] Inventors: Charles Cohen, Medway; Robert A. Dishman, Concord; James S. Huston, Chestnut Hill; Robert L. Bratzler, Concord; David R. Dodds, Millis; Charles M. Zepp, Berlin, all of Mass.

[73] Assignees: Creative BioMolecules, Inc., Hopkinton; Sepracor, Inc., Marlborough, both of Mass.

[21] Appl. No.: 479,935

[22] Filed: Feb. 14, 1990

[51] Int. Cl.[5] .......... B01D 61/28

[52] U.S. Cl. .......... 210/638; 210/644

[58] Field of Search .......... 210/638, 644, 632; 435/7.1, 28

[56] References Cited

U.S. PATENT DOCUMENTS

| | | | |
|---|---|---|---|
| 3,956,112 | 5/1976 | Lee et al. | 210/644 |
| 3,957,504 | 5/1976 | Ho et al. | 210/638 X |
| 4,375,414 | 3/1983 | Strahilevitz | 210/638 |
| 4,859,583 | 8/1989 | Heller et al. | 435/28 X |

*Primary Examiner*—Frank Spear

*Attorney, Agent, or Firm*—Testa, Hurwitz & Thibeault

[57] ABSTRACT

Disclosed are processes and apparatus for separating a desired solute, such as an optically active isomer, from a complex mixture using carrier facilitated transport in an immobilized liquid membrane or carrier facilitated solvent extraction. The carrier is a binding protein selected and/or engineered to immunochemically reversibly bind to the solute and to have a significant solubility in the extracting solvent or immobilized liquid membrane.

12 Claims, 13 Drawing Sheets

26-10 GENES/PROTEINS $V_H$: FR1 | CDR1 | FR2 | CDR2 | FR3 | CDR 3 | FR4

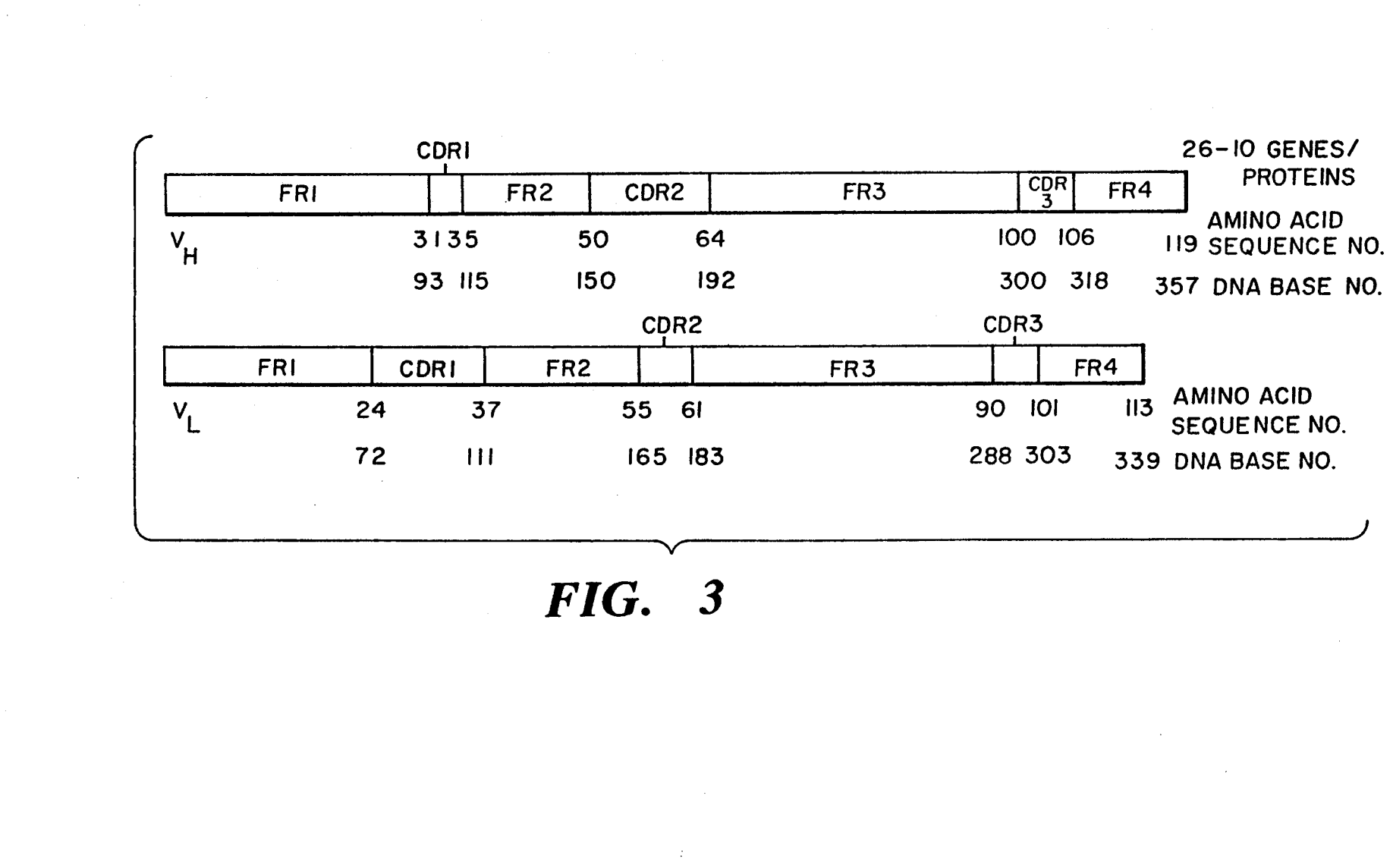

AMINO ACID SEQUENCE NO.: 31 35 50 64 100 106 119

DNA BASE NO.: 93 115 150 192 300 318 357

$V_L$: FR1 | CDR1 | FR2 | CDR2 | FR3 | CDR3 | FR4

AMINO ACID SEQUENCE NO.: 24 37 55 61 90 101 113

DNA BASE NO.: 72 111 165 183 288 303 339

FIG. 3

```
                                                                              FR-1
       10        20        30        40        50        60        70
GAAGTTCAACTGCAGCAGTCTGGTCCTGAATTGGTTAAACCTGGCGCCTCTGTGCGCATGTCCTGCAAATCCTCA
E  V  Q  L  Q  Q  S  G  P  E  L  V  K  P  G  A  S  V  R  M  S  C  K  S  S
          BbvI+       AvaII                   AhaII         HhaI               MnlI+
          Fnu4HI      Sau96I                  BanIMnlI+     HinPI
        PstI                               EcoRII         FspINlIIII
                                              HaeII           NspHI
                                               HhaI
                                               HinPI
                                              NarI
                                              NlaIV
                                           ScrFI

      | X1          FR-2     |         X2  |
      | 85        95        105        115 |       125       135       145
GGGTACCGCCAGTCTCATGGTAAGTCTCTAGACTTTAAAGGTAAGGCGACCCTTACTGTCGACAAATCTTCCTCA
 G  Y  R  Q  S  H  G  K  S  L  D  F  K  G  K  A  T  L  T  V  D  K  S  S  S
 BanI  BstXI  NlaIII     XbaI                                AcoI     MboII-
 KpnI                                    DraI                HincII      MnlI+
 NlaIV                                                       SalI
  RsaI                                                         TaqI
```

FIG. 4-1

```
                 FR-3
       160       170       180       190       200       210       220
ACTGCTTACATGGAGCTGCGTTCTTTGACCTCTGAGGACTCCGCGGTATACTATTGCGCGCGTATCGATTATTGG
 T  A  Y  M  E  L  R  S  L  T  S  E  D  S  A  V  Y  Y  C  A  R  I  D  Y  W
             AluI               DdeI HinfI    AccI       AccII  ClaI       l
       NlaIIIBbvI-         MnlI+MnlI-     AccII            AccII TaqI       s
             Fnu4HI                      NspBII          BssHII
                                         SacII           HhaI
                                                           HhaI
                                                         HinPI
                                                           HinPI

       FR-4
       235       245       255       265
GGCCATGGCGCTAGCGTTACCGTGAGCTCCTAAGGATCC
 G  H  G  A  S  V  T  V  S  S  *  G  S
aIV   HaeII                AluI DdeIBamHI
au96I HhaI                BanIIMstIINlaIV
HaeIII HinPI              Bsp1286    Sau3A
  NcoI   NheI             HgiAI     XhoII
   NlaIII                 SacI
  StyI
```

FIG. 4-2

```
         10        20        30        40        50        60        70
GAATTCATGGCTGACAACAAATTCAACAAGGAACAGCAGAACGCGTTCTACGAGATCTTGCACCTGCCGAACCTG
 E  F  M  A  D  N  K  F  N  K  E  Q  Q  N  A  F  Y  E  I  L  H  L  P  N  L
EcoRI                                     MluI      BglII     BspMI+
                                          XmnI

         85        95        105       115       125       135       145
AACGAAGAGCAGCGTAACGGCTTCATCCAAAGCTTGAAAGACGACCCGTCTCAGAGCGCTAACCTGCTGGCAGAG
 N  E  E  Q  R  N  G  F  I  Q  S  L  K  D  D  P  S  Q  S  A  N  L  L  A  E
                                                            BsMI+          H
                                 HindIII                 Eco47III

        160       170       180       190       200       210       220
GCCAAGAAACTGAACGACGCTCAGGCGCCGAAGAGTGATCCCGAAGTTCAACTGCAGCAGTCTGGTCCTGAATTG
 A  K  K  L  N  D  A  Q  A  P  K  S  D  P  E  V  Q  L  Q  Q  S  G  P  E  L
                                                   PstI
                             NarI

        235       245       255       265       275       285       295
GTTAAACCTGGCGCCTCTGTGCGCATGTCCTGCAAATCCTCTGGGTACATTTTCACCGACTTCTACATGAATTGG
 V  K  P  G  A  S  V  R  M  S  C  K  S  S  G  Y  I  F  T  D  F  Y  M  N  W
          NarI      FspI

        310       320       330       340       350       360       370
GTTCGCCAGTCTCATGGTAAGTCTCTAGACTACATCGGGTACATTTCCCCATACTCTGGGGTTACCGGCTACAA
 V  R  Q  S  H  G  K  S  L  D  Y  I  G  Y  I  S  P  Y  S  G  V  T  G  Y  N
    BstXI                XbaI                     PflMI     BstEII

        385       395       405       415       425       435       445
CAGAAGTTTAAAGGTAAGGCGACCCTTACTGTCGACAAATCTTCCTCAACTGCTTACATGGAGCTGCGTTCTTTG
 Q  K  F  K  G  K  A  T  L  T  V  D  K  S  S  S  T  A  Y  M  E  L  R  S  L
    DraI                        SalI

        460       470       480       490       500       510       520
ACCTCTGAGGACTCCGCGGTATACTATTGCGCGGGCTCCTCTGGTAACAAATGGGCCATGGATTATTGGGGTCAT
 T  S  E  D  S  A  V  Y  Y  C  A  G  S  S  G  N  K  W  A  M  D  Y  W  G  H
                                                         NcoI
           SacII
```

FIG. 5-1

```
         535         545         555         565         575         585         595
GGTGCTAGCGTTACTGTGAGCTCTGGTGGCGGTGGGTCGGGCGGTGGTGGCTCGGGTGGCGGCGGATCCGACGTC
 G  A  S  V  T  V  S  S  G  G  G  G  S  G  G  G  G  S  G  G  G  G  S  D  V
                                                                BamHI AatII
   NheI
                SacI

         610         620         630         640         650         660         670
GTTGTTACCCAGACTCCGCTGTCTCTGCCGGTTTCTCTGGGTGACCAGGCTTCTATTTCTTGCCGCTCTTCCCAG
 V  V  T  Q  T  P  L  S  L  P  V  S  L  G  D  Q  A  S  I  S  C  R  S  S  Q
                                         BstEII                          PflM

         685         695         705         715         725         735         745
TCTCTGGTCCATTCTAATGGTAACACTTACCTGAACTGGTACCTGCAAAAGGCTGGTCAGTCTCCGAAGCTTCTG
 S  L  V  H  S  N  G  N  T  Y  L  N  W  Y  L  Q  K  A  G  Q  S  P  K  L  L
I
          BstXI                          BspMI+                     HindIII
                                           KpnI

         760         770         780         790         800         810         820
ATCTACAAAGTCTCTAACCGCTTCTCTGGTGTCCCGGATCGTTTCTCTGGTTCTGGTTCTGGTACTGACTTCACC
 I  Y  K  V  S  N  R  F  S  G  V  P  D  R  F  S  G  S  G  S  G  T  D  F  T

         835         845         855         865         875         885         895
CTGAAGATCTCTCGTGTCGAGGCCGAAGACCTGGGTATCTACTTCTGCTCTCAGACTACTCATGTACCGCCGACT
 L  K  I  S  R  V  E  A  E  D  L  G  I  Y  F  C  S  Q  T  T  H  V  P  P  T
   BglII

         910         920         930         940
TTTGGTGGTGGCACCAAGCTCGAGATTAAACGTTAACTGCAG
 F  G  G  G  T  K  L  E  I  K  R  *
                 XhoI
                              HpaI PstI
```

FIG. 5-2

```
        10        20        30        40        50        60
GATCCTGACGTCGTAATGACCCAGACTCCGCTGTCTCTGCCGGTTTCTCTGGGTGACCAG
 D  P  D  V  V  M  T  Q  T  P  L  S  L  P  V  S  L  G  D  Q
      AatII                                           BstEII

        70        80        90       100       110       120
GCTTCTATTTCTTGCCGCTCTTCCCAGTCTCTGGTCCATTCTAATGGTAACACTTACCTG
 A  S  I  S  C  R  S  S  Q  S  L  V  H  S  N  G  N  T  Y  L
                        PflMI     BstXI

       130       140       150       160       170       180
AACTGGTACCTGCAAAAGGCTGGTCAGTCTCCGAAGCTTCTGATCTACAAAGTCTCTAAC
 N  W  Y  L  Q  K  A  G  Q  S  P  K  L  L  I  Y  K  V  S  N
       BspMI+                      HindIII
    KpnI

       190       200       210       220       230       240
CGCTTCTCTGGTGTCCCGGATCGTTTCTCTGGTTCTGGTTCTGGTACTGACTTCACCCTG
 R  F  S  G  V  P  D  R  F  S  G  S  G  S  G  T  D  F  T  L

       250       260       270       280       290       300
AAGATCTCTCGTGTCGAGGCCGAAGACCTGGGTATCTACTTCTGCTCTCAGACTACTCAT
 K  I  S  R  V  E  A  E  D  L  G  I  Y  F  C  S  Q  T  T  H
 BglII

       310       320       330       340       350       360
GTACCGCCGACTTTTGGTGGTGGCACCAAGCTCGAGATTAAACGTGGATCTGGAGGTGGC
 V  P  P  T  F  G  G  G  T  K  L  E  I  K  R  G  S  G  G  G
                               XhoI

       370       380       390       400       410       420
GGATCTGGTGGAGGTGGCTCTGGTGGCGGTGGATCCGAAGTTCAATTGCAGCAGTCTGGT
 G  S  G  G  G  G  S  G  G  G  G  S  E  V  Q  L  Q  Q  S  G
                               BamHI

       430       440       450       460       470       480
CCTGAATTGGTTAAACCTGGCGCCTCTGTGCGCATGTCCTGCAAATCCTCTGGGTACATT
 P  E  L  V  K  P  G  A  S  V  R  M  S  C  K  S  S  G  Y  I
                   NarI     FspI

       490       500       510       520       530       540
TTCACCGACTTCTACATGAATTGGGTTCGCCAGTCTCATGGTAAGTCTCTAGACTACATC
 F  T  D  F  Y  M  N  W  V  R  Q  S  H  G  K  S  L  D  Y  I
                              BstXI             XbaI
```

*FIG. 6-1*

```
        550        560        570        580        590        600
GGGTACATTTCCCCATACTCTGGGGTTACCGGCTACAACCAGAAGTTTAAAGGTAAGGCG
 G  Y  I  S  P  Y  S  G  V  T  G  Y  N  Q  K  F  K  G  K  A
             PflMl       BstEII                 DraI

        610        620        630        640        650        660
ACCCTTACTGTCGACAAATCTTCCTCAACTGCTTACATGGAGCTGCGTTCTTTGACCTCT
 T  L  T  V  D  K  S  S  S  T  A  Y  M  E  L  R  S  L  T  S
          SalI

        670        680        690        700        710        720
GAGGACTCCGCGGTATACTATTGCGCGGGCTCCTCTGGTAACAAATGGGCCATGGATTAT
 E  D  S  A  V  Y  Y  C  A  G  S  S  G  N  K  W  A  M  D  Y
        SacII                                      NcoI

        730        740        750        760
TGGGGTCATGGTGCTAGCGTTACTGTGAGCTCTTAACTGCAG
 W  G  H  G  A  S  V  T  V  S  S  *
```

*FIG. 6-2*

```
                                        10                                                                      20
Met Lys Ala Ile Phe Val Leu Lys Gly Ser Leu Asp Arg Asp Leu Asp Ser Arg Leu Asp
ATG AAA GCA ATT TTC GTA CTG AAA GGT TCA CTG GAC AGA GAT CTG GAC TCT CGT CTG GAT
                                                      BglII
                                        30                                                                      40
Leu Asp Val Arg Thr Asp His Lys Asp Leu Ser Asp His Leu Val Leu Val Asp Leu Ala
CTG GAC GTT CGT ACC GAC CAC AAA GAC CTG TCT GAT CAC CTG GTT CTG GTC GAC CTG GCT
                                            BclI                SalI
                                        50                                                                      60
Arg Asn Asp Leu Ala Arg Ile Val Thr Pro Gly Ser Arg Tyr Val Ala Asp Leu Glu Phe
CGT AAC GAC CTG GCT CGT ATC GTT ACT CCC GGG TCT CGT TAC GTT GCG GAT CTG GAA TTC
                                    SmaI                                        EcoRI

Asp
GAT
```

*FIG. 9*

SEPARATION BY CARRIER MEDIATED TRANSPORT

BACKGROUND OF THE INVENTION

This invention relates to separation of individual solutes from a mixture. More specifically, the invention relates to exploitation of carrier mediated transport mechanisms in immobilized liquid membrane and related separation systems.

There is a continuing need for more efficient methods of separating the solutes in mixtures of structurally related bioactive compounds. Synthesis of bioactive materials such as pharmaceuticals and pesticides using organic chemistries often requires separations on a preparative scale. The products of expression of engineered microorganisms and cell lines typically comprise a single valuable species in admixture with a host of extraneous proteins, lipids, nucleic acids, and polysaccharides. Isolation of pure or substantially pure product on a commercial scale from such mixtures presents a significant engineering challenge. Chromatography, differential precipitation, filtration, and other separation technologies are used to remove selectively unwanted species. Often, the late-purification stages are most difficult and can be achieved only by means of affinity chromatography using polyclonal or monoclonal antibodies which selectively immunochemically bind with the product.

Molecular biology has advanced as a technology sufficient to permit production of a variety of valuable biologically active proteins Pending U.S. application Ser. Nos. 052,800 and 342,449, and PCT Application US88/01737, disclose biosynthetic multifunctional proteins comprising plural bioactive domains, one of which is capable of binding to a preselected compound. The binding domain is patterned after the antibody binding site and can mimic the binding properties of a light or heavy chain protein, or comprises a single chain construct comprising both light and heavy chains. Such constructs may be used in affinity chromatography procedures and may have significant cost advantages over monoclonal antibodies.

Among the most difficult purification tasks is the separation of stereoisomers. Many organic compounds exist in optically active forms, i.e., they have the ability to rotate the plane of plane polarized light. In describing an optically active compound, the prefixes D and L, or R and S are used to denote the absolute configuration of the molecule about its chiral center(s). The prefixes designate the sign of rotation of plane polarized light by the compound, with (−) or L meaning that the compound is levorotatory. For a given chemical structure, D and L stereoisomers are mirror images of one another. A specific stereoisomer may also be referred to as an enantiomer, and a mixture of such isomers is often called an enantiomeric or racemic mixture. The term "racemic mixture" as used herein, refers to a mixture of at least first and second stereoisomers in any proportion.

Optical activity is typically the result of molecular asymmetry about tetrahedral carbon atoms that are linked to four different moieties. Where there is only one asymmetric carbon atom, or "chiral center", there are two possible stereoisomers or enantiomers. Where there are n chiral centers, the number of potential stereoisomers increases to $2^n$. The structural differences between stereoisomers are subtle and of little consequence in ordinary chemical reactions, and this accounts for many of the difficulties encountered in resolving racemic mixtures. However, these small structural differences may be profound in biological systems, e.g., if the compounds are involved in enzyme-catalyzed reactions or bind specifically to cellular receptors. Thus, the L-amino acids are metabolized in humans but the corresponding D analogs are not. Only D-glucose can be phosphorylated and processed into glycogen or degraded by the glycolytic and oxidative pathways of intermediary metabolism. Similarly, beta blockers, pheromones, prostaglandins, steroids, flavoring and fragrance agents, pharmaceuticals, pesticides, herbicides, and many other compounds exhibit critical stereospecificity. In the field of pesticides, for example, Tessier has shown that only two of the eight stereoisomers of deltamethrin, a pyrethroid insecticide, have any biological activity. (Chemistry and Industry, Mar. 19, 1984, p. 199). Other forms of optical isomers are known which are of commercial interest.

Stereochemical purity is also important in the field of pharmaceuticals, where 12 of the 20 most prescribed drugs exhibit chirality. A case in point is provided by naproxen, or (+) S-2-(6-methoxy-2-naphthyl) propionic acid, used for instance in the management of arthritis. In this case, the S(+) enantiomer of the drug is known to be 28 times more therapeutically potent than its R(−) counterpart. Still another example of chiral pharmaceuticals is provided by the family of beta-blockers; the L-form of propranolol is known to be 100 times more potent than the D-enantiomer.

Synthesis of chiral compounds by standard organic synthetic techniques generally leads to a racemic mixture which, in the aggregate, may have a relatively low specific bioactivity since certain of the stereoisomers in the mixture are likely to be biologically or functionally inactive. As a result, relatively larger quantities of the material must be used to obtain an effective dose, and manufacturing costs are increased due to the co-production of stereochemically "incorrect" and hence, inactive ingredients. Also, the inactive enantiomer may have unwanted side effects.

A widely used approach to purifying optical isomers is the selective precipitation of the desired compound from a racemic mixture. See, for example, U.S. Pat. No. 3,879,451, 4,257,976, 4,151,198, 4,454,344; Harrison et al, J. Med. Chem. 13:203 (1970); Felder et al, UK Patent Application No. GB2025968A (1980), and U.S. 4,285,884. Separation of diastereomers also can be carried out by chromatography. See, for example, Pollock et al, J. Gas Chromatogr. 3:174 (1965); Mikes et al, J. Chromatogr. 112:205 (1976); and Hare et al, U.S. Pat. No. 4,290,893. Enzymes have been used for the resolution of stereoisomers on a preparative scale. For instance, enzymatic treatment has been applied to the resolution of racemic mixtures of amino esters. See U.S. Pat. No. 3,963,573, U.S. Pat. No. 4,262,092, Clement and Porter, J. Chem. Ed., 48:695 (1971), and Matta et al J. Org. Chem., 39:2291 (1974). Additional examples of enzyme-mediated resolution as applied to the production of optically purified pharmaceuticals include Sih U.S. Pat. No. 4,584,370, Aragozzini et al, Biotechnol Letters, 8:95 (1980), Yokozeki et al, EPO No. 0 122 794 A2, and Sih, Tetrahedron Letters, 27:1763 (1986). Multiphase and extractive enzyme membrane bioreactors that selectively produce pure or substantially purified optically active compounds from achiral precursors or mixtures are disclosed by Matson in U.S. Pat. No.

4,800,162. The term "resolution" as used herein, refers to separation of a first mixture into second and third mixtures wherein the proportions of the solutes in the second and third mixtures are different from that in the first mixture, the proportion being greater in one and necessarily smaller in the other.

Permeation of solutes through liquids has been exploited for separation of certain ions using an immiscible liquid film as a membrane to mediate transport. In these so-called "immobilized liquid membranes", a microporous solid support holds the liquid as a continuous barrier between the feed and product streams. The liquid is held in place by capillarity and assumes the geometry of the support. A novel variation of this technology exploits coupled transport. An extracting agent in the membrane selectively complexes a metal iön in the feedstream, then diffuses across the membrane and releases the ion into a stripping stream. Regenerated, the extracting agent then shuttles back to the feed side of the membrane to repeat the process. The acidity of the feed and stripping streams is adjusted to favor complexation and decomplexation reactions at the solution-membrane interfaces and to provide a concentration gradient of the coupling ion as a driving force. Typical coupled transport modules are constructed using hollow fibers with diameters on the order of 100 to 1000 μm and are used, for example, to recover metals from plating wastes.

The primary object of this invention is the provision of apparatus and processes for the rapid separation of solutes useful in preparative contexts to resolve complex mixtures including solutions of proteins and isomeric or racemic mixtures, and can be scaled readily to permit any desired throughput. Another object is to provide such apparatus and processes that can be adapted to purify any unique species, provided only that the species is capable of being uniquely reversibly complexed by a proteinaceous binding site.

SUMMARY OF THE INVENTION

This invention provides processes and systems for separating a preselected solute in a solution comprising a mixture of solutes which exploits carrier mediated transport in immobilized liquid membranes or membrane solvent extractors. The processes are useful in the production of many pure organic compounds including various proteins, and polypeptides, nonprotein pharmaceuticals, fragrances, flavoring agents, agricultural chemicals such as pesticides and herbicides, and other chemical classes. The invention finds perhaps its optimal use in the resolution of racemic mixtures to produce pure or substantially purified optically active organic acids, alcohols, esters, amides, amines, nitriles, hydantoins, and other chiral compounds.

In its broadest aspects the invention comprises apparatus for separating a solute from a mixture. The apparatus comprises a porous membrane, a liquid phase in contact with the membrane, and means for passing a feed solution into interactive contact with the liquid phase at an interface on a surface of or within the membrane. The feed solution comprises a mixture including the solute to be separated disposed in a solvent substantially immiscible with the liquid phase. Dissolved in the liquid phase is a binding protein which is substantially insoluble in the feed solution. The binding protein has a binding specificity for the solute in preference to other solutes in the feed and reversibly immunochemically binds the solute. The phrase "immunochemical bond" as used herein, unless antithetical to its context, refers broadly to reversible binding of the type that is ubiquitous in biological systems. It is not limited to classical antigen-antibody complex formation but rather includes ligand receptor interactions, enzyme substrate interactions, and other protein-protein bindings or associations involving complementary stereochemical interfit, charge pairing, hydrogen bonding, and thermodynamic interactions.

In one embodiment, the liquid phase is immobilized within the membrane, and the apparatus includes means for passing a product stream into reactive contact with the liquid phase at a second interface at the membrane opposite the first interface. The product stream serves to dissolve the solute at the second interface as the complex of the solute and the binding protein dissociates. The mass action at the interfaces and diffusion between them result in the creation of concentration gradients across the immobilized liquid membrane favoring diffusion of the binding protein/solute complex from the feed interface to the product interface, and diffusion of the uncomplexed binding protein in the reverse direction.

In another embodiment, the apparatus comprises a second membrane, the liquid phase is in contact with both membranes, and the apparatus includes means for circulating the liquid phase convectively between the interfaces at the respective membranes such as a pump. A product stream in interactive contact with the second membrane collects product as the binding protein/solute complex dissociates.

In preferred aspects, the binding protein is a biosynthetic construct having a binding domain which mimics the structure of one or both of the protein chains defining the binding pocket of an immunoglobulin. The construct may comprise a second domain for imparting optimal solubility properties to the binding protein in the liquid phase. Preferably, the binding protein is constructed as disclosed herein so as to have a high specificity for the solute of interest and an appropriate affinity. This approach facilitates association and dissociation at the reactive interfaces and promotes high resolution. In a preferred embodiment, the liquid phase is aqueous, or at least hydrophilic, and the product and feed streams are hydrophobic.

These and other objects and features of the invention will be apparent from the drawing, description, and claims which follow.

BRIEF DESCRIPTION OF THE DRAWING

FIG. 3 is a schematic drawing of the structure of Fv proteins (and DNA encoding them) illustrating $V_H$ and $V_L$ domains, each of which comprises four framework regions (FR) and three complementarity determining regions (CDR). Boundaries of CDRs are indicated, by way of example, for monoclonal 26-10, a well known and characterized murine monoclonal specific for digoxin.

FIG. 4 is the nucleic acid and encoded amino acid sequence of a host DNA ($V_H$) designed to facilitate insertion of CDRs of choice. The DNA was designed to have unique 6-base sites directly flanking the CDRs so that relatively small oligonucleotides defining portions of CDRs can be readily inserted, and to have other sites to facilitate manipulation of the DNA to optimize binding properties in a given construct. The framework regions of the molecule correspond to murine FRs.

FIGS. 5 and 6 are multifunctional proteins (and DNA encoding them) comprising a single chain biosynthetic antibody binding site (BABS) construct with the specificity of murine monoclonal 26-10, linked through a spacer to the FB fragment of protein A, here fused as a leader. The Eco RI site is not part of the expressed chain, and the MET residue 1 is removed in vivo in *E. coli* expression. The spacer comprises the 11 C-terminal amino acids of the FB followed by Ser-Asp-Pro (a dilute acid cleavage site). The single chain BABS comprises sequences mimicking the $V_H$ and $V_L$ (5) and the $V_L$ and $V_H$ (6) of murine monoclonal 26-10. The $V_L$ in construct 5 is altered at residue 4 where valine replaces methionine present in the parent 26-10 sequence. These constructs contain a binding site for digoxin and its analogs and a leader which promotes water solubility. Their structure may be summarized as;

Figure 1:
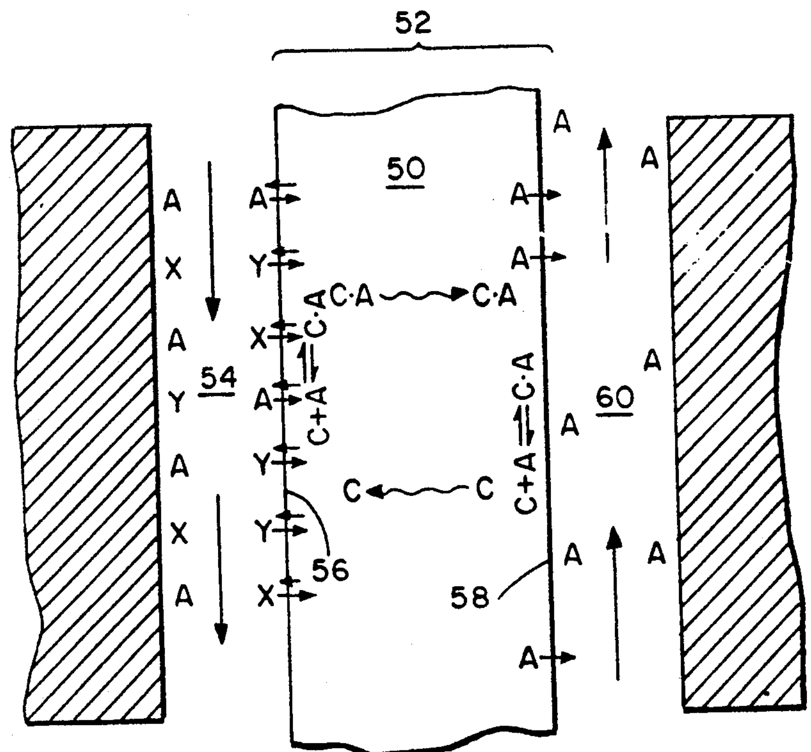
FIG. 1 is a schematic illustration of a first embodiment of the system and process of the invention which exploits diffusive transport of binding protein and binding protein/solute complex.

(5) FB—Asp—Pro—$V_H$—($Gly_4$—Ser)$_3$—$V_L$, and (6) FB—Asp—Pro—$V_L$—($Gly_4$—Ser)$_3$—$V_H$, where ($Gly_4$-Ser)$_3$ is a polypeptide linker.

In FIGS. 5, the amino acid sequence of the expression product starts after the GAATTC sequence, which codes for an EcoRI splice site, translated as Glu-Phe on the drawing.

Figure 7A:
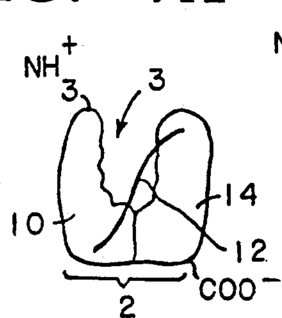
Figure 7B:
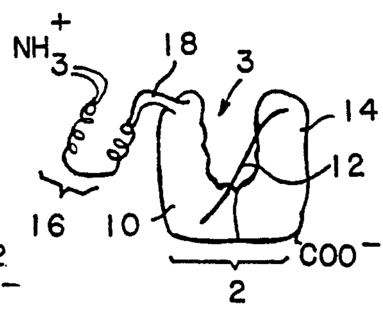
Figure 8:
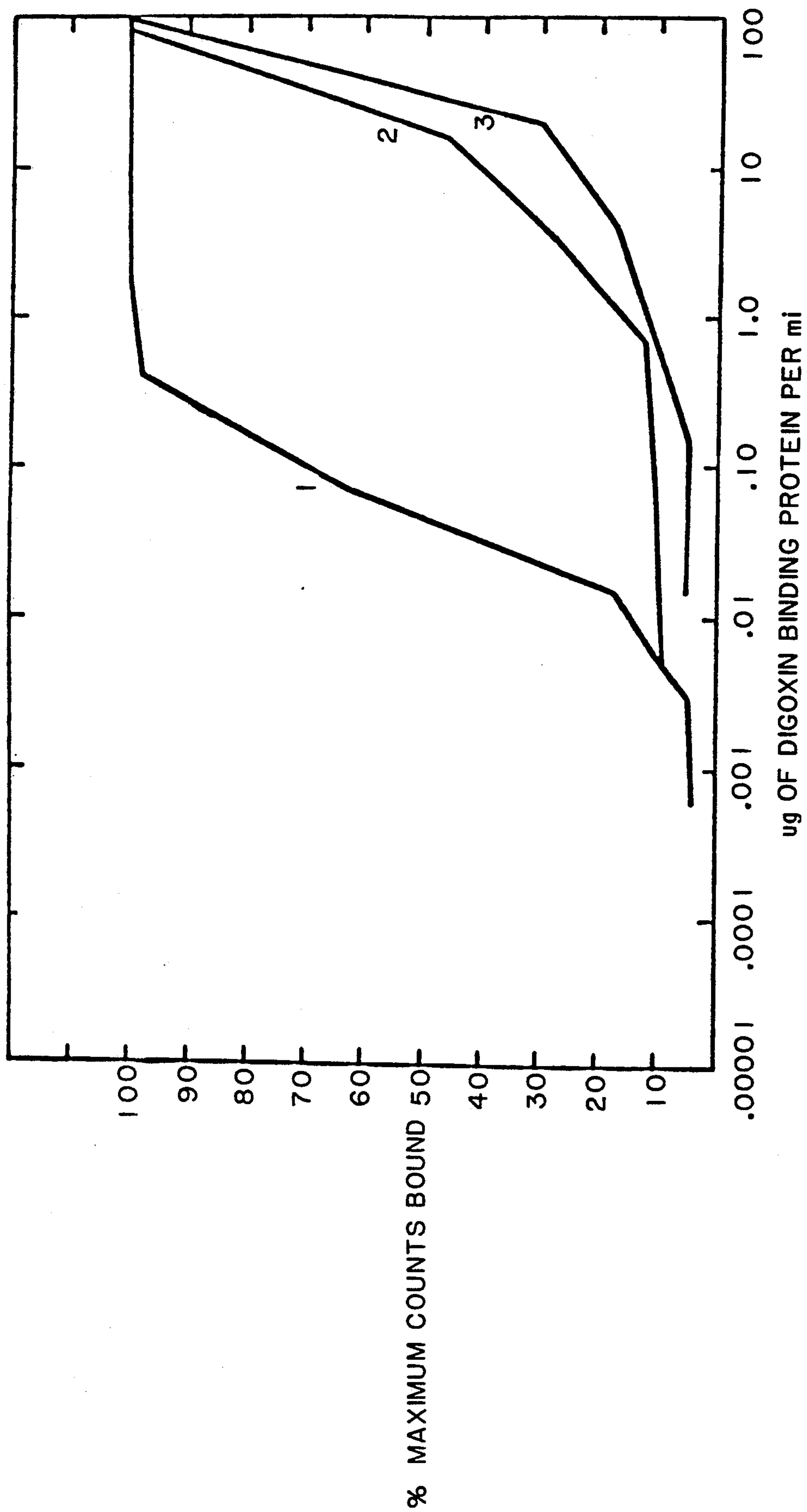

FIGS. 7A-7D are schematic representations of some of the classes of binding proteins useful in the apparatus and process of the invention;

FIG. 8 is a graph of percent of maximum counts bound of radioiodinated digoxin versus concentration of binding protein adsorbed to the plate comparing the binding of native 26-10 (curve 1) and the construct of FIG. 5 and FIG. 7B renatured using two different procedures (curves 2 and 3).

Figure 10:
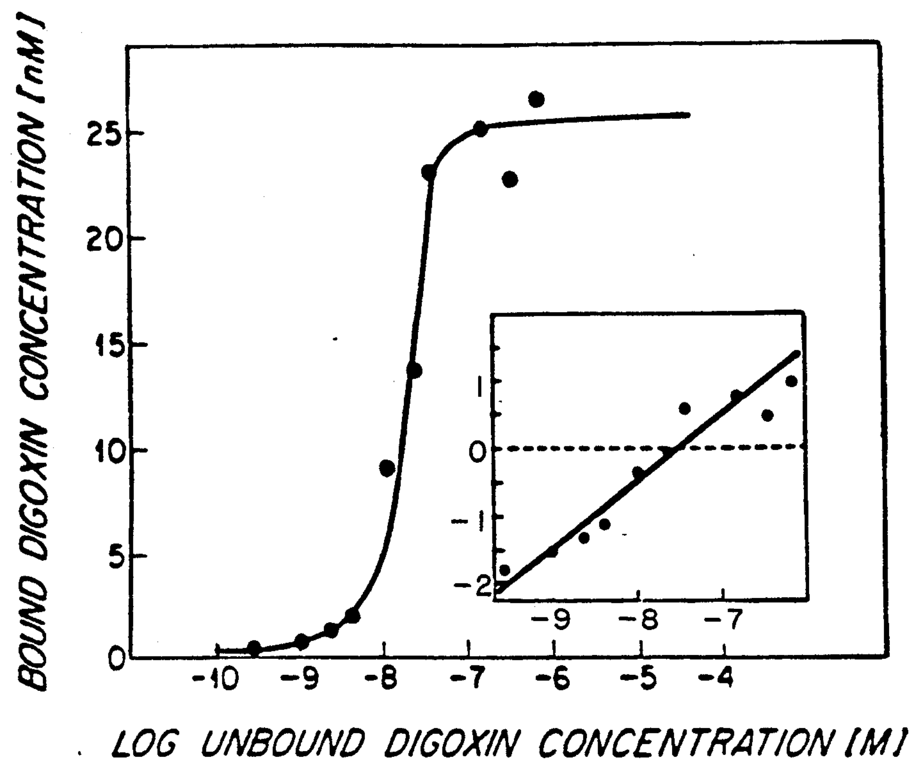
Figure 11:
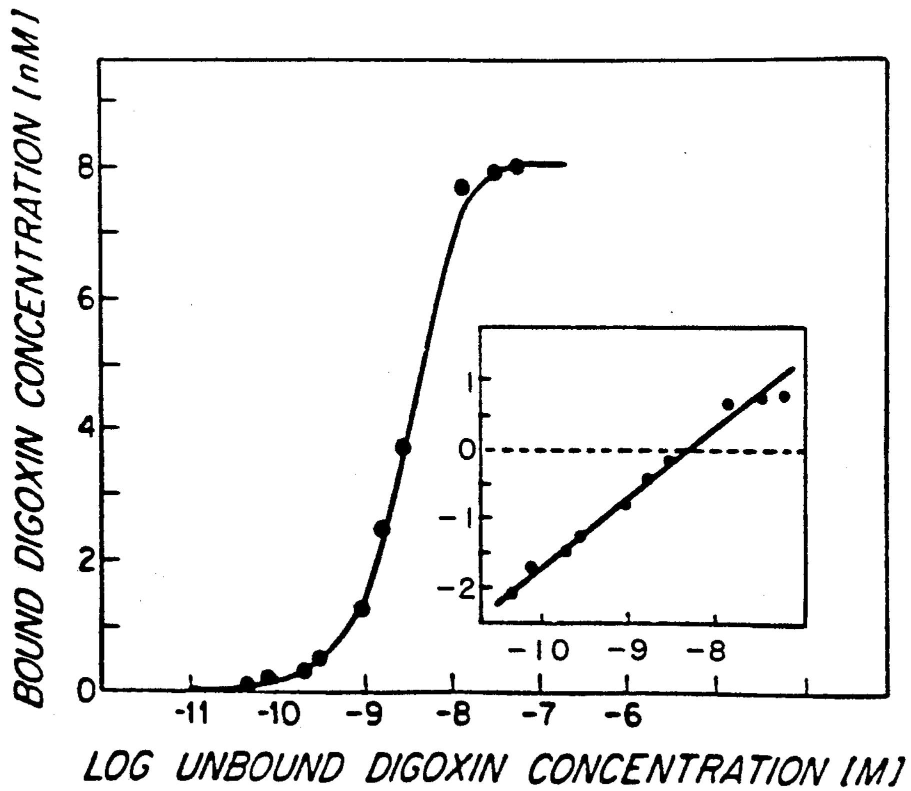
Figure 12:
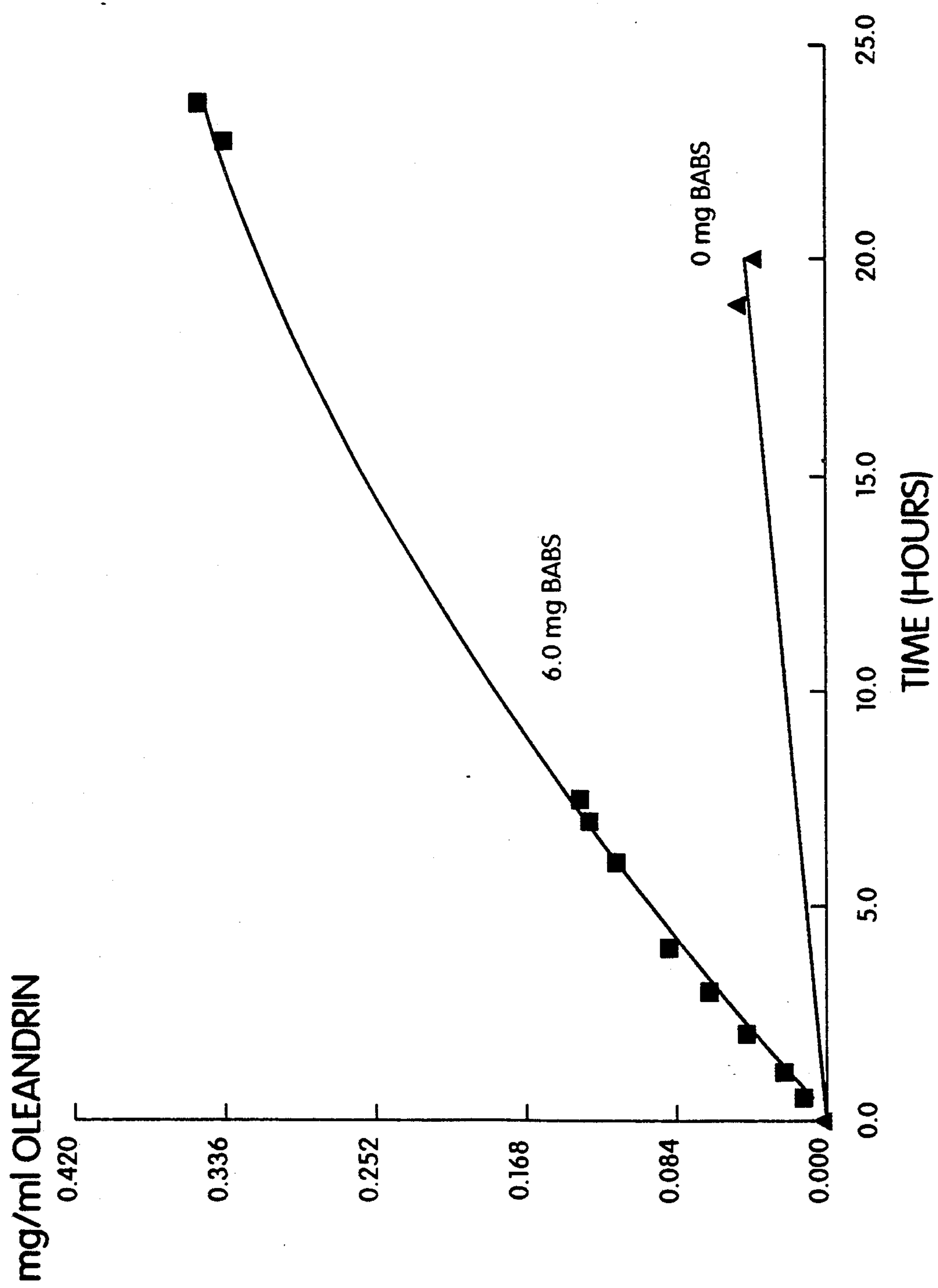

FIG. 9 is a schematic representation of the DNA and amino acid sequence of a leader peptide (MLE) protein with corresponding DNA sequence and some major restriction sites;

FIGS. 10 and 11 are plots of digoxin binding curves. (A) shows 26-10 BABS binding isotherm and Sips plot (inset), and (B) shows 26-10 Fab binding isotherm and Sips plot (inset); and FIG. 12 is a graph of product stream solute concentration vs. time illustrating the effect on transport across a liquid membrane of the presence of a protein which binds the solute reversibly.

Like reference characters in the respective drawn figures indicate corresponding parts.

DESCRIPTION

This invention combines certain features of heretofore disparate technologies to advance the art of separation and purification of valuable chemicals such as pesticides, biologicals, and drugs, with particular reference to the resolution of racemic or other types of isomeric mixtures. Practical application of the invention is made possible by the development of recombinant DNA techniques to produce proteins, cassette mutagenesis techniques, analysis of function-structure relationships, and other technologies of the type disclosed herein. These techniques permit the production of binding proteins useful in the context of this invention and optionally having solubility and binding properties which optimize the processes disclosed herein.

Approaches to exploiting the unique properties of such synthetic binding proteins in practical separation processes necessarily involve membrane contacting-/separating steps. In particular, microporous membrane systems used in immobilized liquid membrane and membrane solvent extraction separation techniques comprise preferred process configurations. These membrane-based separation processes provide efficient methods for bringing into simultaneous contact three liquid solutions: (i) the feed liquid stream comprising the mixture of solutes to be processed, (ii) the solution of binding protein which exhibits binding selectivity towards the particular solute to be recovered and purified, and (iii) the product stream in which the selected solute is to be recovered. Major design objectives of such systems are to promote rapid solute transfer between the solutions while confining the binding protein to prevent its loss. At the same time, the unique physical and chemical properties of synthetic binding proteins make technically and economically feasible liquid membrane and solvent extraction based processes that otherwise have little utility in these difficult separation tasks. It is this uniquely effective combination of novel attributes of certain types of liquid membrane and solvent extraction technology together with certain properties of synthetic binding proteins that is the basis for the present invention.

A particularly important category of separation processes of the invention involves optical resolution, i.e., the separation of a particular stereoisomer or enantiomer from a mixture of such stereoisomers. Here, the ability to rationally design and produce a synthetic binding protein which simultaneously exhibits both desirable binding properties (e.g., selectivity at the chiral center with appropriate physical properties such as size and solubility) provides a powerful means of obtaining chiral selector molecules for use in any given optical resolution process. At the same time, the use of such enantioselective binding proteins becomes practical by their incorporation into membrane-based processes of the types described below.

Referring to FIG. 1 an immobilized liquid membrane 50 consists of a microporous, typically polymeric support membrane 52 impregnated with a liquid phase which is retained in the pores of the support 50 by capillary action. Such liquid membranes combine the desirable permeation properties of the liquid phase, such as high permeant solubility and diffusivity, with the mechanical properties and geometry of the microporous support membrane. Opposite sides of the liquid membrane 50 are served by feed stream 54 and product stream 60, both of which are immiscible with liquid phase 50. A reversibly reactive binding protein which acts as a carrier species (C) is dissolved within the liquid membrane thereby permitting operation of a chemically selective process here described as carrier mediated transport. In such transport, as schematically illustrated in FIG. 1, a carrier species C, comprising a binding protein, is dissolved in the solvent disposed in the support membrane 52. The carrier C reacts reversibly with a particular solute of interest (A) from the feed stream 54 to form a membrane soluble complex (CA) at the interface 56 of the liquid membrane 50 and feed stream 54. Various species (A,X,Y) from feed stream 54 enter liquid membrane 50. Some fraction of these diffuse across membrane 50, traverse liquid membrane/product stream interface 58, and enter product stream 60. The presence of complex C which sequesters solute A produces a driving force for solute A to enter the liquid membrane.

Under the influence of diffusion, the complex CA forms a concentration gradient across liquid membrane 50. At interface 58, where the local concentration of free solute A is lowest, the complex dissociates, thereby allowing the transported solute to partition into and to be removed by a product stream 60 across the interface 58. Because complex formation is involved in the transport process, the selectivity can be high. Further, if the carrier is isomer/enantiomer selective, then the process is capable of performing chiral separations.

Figure 2:
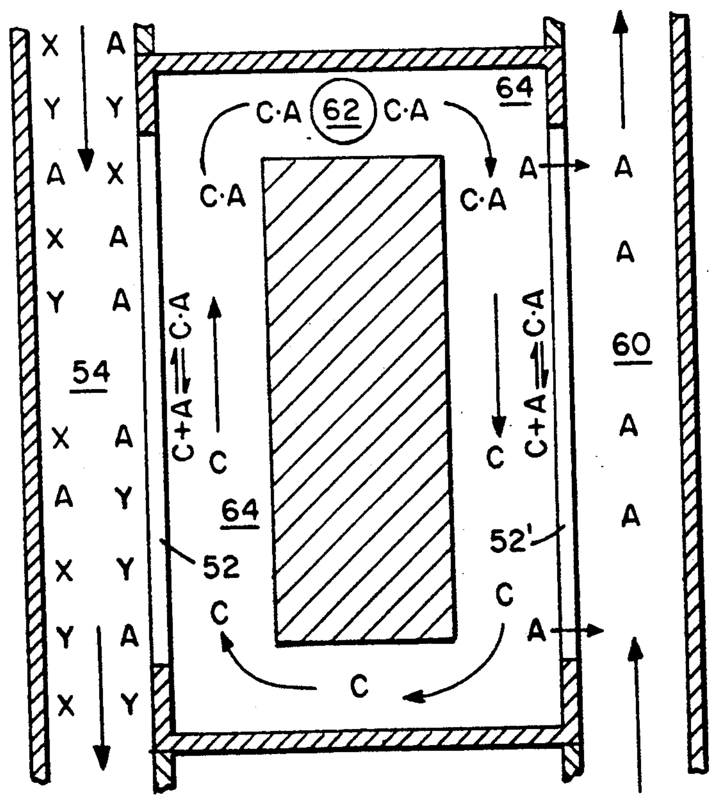
FIG. 2 is a schematic illustration of a second embodiment of the system and process of the invention which exploits convective transport of binding protein and binding protein/solute complex.

Another embodiment of the invention is schematically depicted in FIG. 2. This embodiment is based on circulating a solution of binding protein between two membrane separators 52, 52' by convection using pump 62 as opposed to diffusion through an immobilized liquid membrane. In this instance, the membrane separators 52, 52' serve the purpose of providing emulsion and entrainment-free liquid/liquid contacting area between the feed stream 54 and circulating liquid phase 64 and between the liquid phase 64 and product stream 60 while at the same time geometry is referred to herein as solvent extraction. The essential principles of the system are similar to that of FIG. 1 except that diffusive transport of complex CA and diffusive return of complex C across the liquid membrane 50 of FIG. 1 is replaced by convective circulation between membranes 52 and 52'.

Immobilized liquid membranes and solvent extraction systems may be based on either aqueous or organic solutions, depending on what type of solution preferentially "wets" the membrane, i.e., depending on whether the microporous support membrane 52 (and 52') is hydrophilic or hydrophobic, and depending on the nature of the feed stream and solute to be separated. Both aqueous-based and organic-based membranes are of interest in the practice of this invention. Because some of the particulars of their use differ, the two types of systems are discussed separately below.

Having described the general nature of the immobilized liquid membrane and solvent extraction processes, each will now be discussed in greater detail.

Most non-membrane proteins and "engineered" synthetic binding proteins are more water-soluble than they are organic-soluble and operate naturally in an aqueous milieu. The situation where the membrane is hydrophilic and serves to immobilize an aqueous solution of binding protein will be described first.

Membranes

Preferred polymers from which hydrophilic microporous membranes may be fabricated include but are not limited to regenerated cellulose, cellulose esters, polyacrylonitrile and copolymers thereof (especially the hydrophilic ones including but not limited to copolymers incorporating acrylamide, acrylate, and/or methacrylate functionalities), polyurethane-containing copolymers, and blends with the polyarylsulfones and polyarylethersulfones (more particularly, polysulfone and polyethersulfone, and blends thereof with such hydrophilic copolymers as polyethylene-oxide, polyethyleneglycol, and polyvinyl-alcohol). In addition to its wettability by aqueous solutions, another important property of the membrane polymer will be its chemical resistance to such organic solvents as may contact it during the process of the invention.

The morphologies or microstructures characteristic of membranes suitable as immobilized liquid membrane supports and solvent extraction membranes include those typical of both microfiltration and ultrafiltration membranes. Microfiltration membranes typically possess pores ranging in diameter from about 0.01 μm to about 10 μm, preferably about 0.02 μm to 2 μm. Microfiltration membranes frequently are isotropic, i.e., have a fairly uniform pore size across the thickness of the membrane. In contrast, ultrafiltration membranes are asymmetric and are typically characterized by a thin "skin" layer on the order of 0.1 to 0.2 μm in thickness, supported atop a much thicker (100 to 200 μm) and highly porous substrate region. The skin of such asymmetric ultrafiltration membranes typically has pore sizes in the range of about 1 to about 200 nm. Finally, asymmetric membranes that combine the features of the "skin" typical of ultrafiltration membranes with the more nearly isotropic "substrate" region typical of microfiltration membranes will also be suitable and in some cases preferable in the practice of the invention. All of these suitable membrane types are referred to herein simply as "microporous".

The geometry of the support membrane, i.e., flat sheet, tubular, hollow fiber, or other, is not critical to the invention. It is essential only that the membrane have two surfaces, each of which may be contacted in a continuous fashion with separate process streams. Modules containing large numbers of hollow fibers will frequently be preferred since the hollow-fiber geometry provides a high surface area membrane in a compact package at low cost. Finally, the present invention will be workable over a broad range of membrane thicknesses—e.g., from about 5 to about 500 μm. In general, thinner membranes provide higher transmembrane fluxes of the solute to be separated from the mixture, but also are more difficult to manufacture, handle, and maintain in working condition. From a practical viewpoint, membranes useful in the practice of this invention typically will be from about 10 to about 100 μm thick.

Immobilized liquid membranes may be impregnated or loaded with liquid simply by contacting the microporous support in its dry condition with a solution capable of wetting its pores. For instance, membrane liquid may be supplied to the lumen- and/or shell side compartments in a hollow-fiber membrane module, with the result that capillarity will draw liquid into the pores of the initially dry support membrane. Excess liquid may then be removed from the surface of the membrane by a flushing procedure, and immiscible liquid process streams then may be introduced to the lumen and shell compartments.

The liquid in the hydrophilic immobilized liquid membrane will be an aqueous solution of a preferentially water-soluble binding protein. The binding protein is chosen, designed, and synthesized so as to be capable of selectively forming a complex with the particular "target" solute (or group of solutes) to be separated from the mixture. The binding protein serves as the "carrier" species in a process of carrier-mediated transport which operates within the immobilized liquid membrane or solvent extraction apparatus as generally disclosed above. Where the binding protein is capable of binding enantioselectively to a single stereoisomer in a mixture (e.g., a racemic mixture or 50:50 mixture of two stereoisomers), it serves as a chiral selector and carrier in a facilitated transport process capable of effecting an optical resolution of chiral solutes. The specifications of and means for obtaining binding properties of a binding protein useful as a "carrier" molecule in the process of the present invention are discussed in some detail below.

Feed Solutions, Product Solvents, and Operational Parameters

Many of the solutes which can be separated by the process of the present invention are relatively hydrophobic (lipophilic), and thus are preferentially soluble in organic solutions. Indeed, many of the chiral pharmaceuticals and biomolecules that one may seek to resolve exhibit limited water solubility. However, as discussed in more detail below, this is an advantage in a properly designed system.

It is not possible to provide a comprehensive list of the materials that can be separated using the process and apparatus of the invention. Generally, the only requirement is that the material be soluble in some hydrophilic or hydrophobic solvent and have molecular features that can be recognized by a binding protein.

Where one or more of the solutes in a mixture exists as a solid at the temperature and pressure of separation, it will be convenient to dissolve the mixture in a water-immiscible organic solvent for feeding to the membrane separator in the form of a homogeneous solution. Alternatively, in the case where the solute mixture (e.g., a racemic mixture) exists as a water-immiscible liquid at separation process conditions, the mixture may be supplied as the neat organic liquid or liquid mixture. The term "solute", as used in the description hereafter and in the claims, is intended to embrace such organic liquids. In both cases, it is critical to the operation of the invention that the organic-phase feed mixture be essentially immiscible with the aqueous solution of synthetic binding protein contained within the pores of the immobilized liquid membrane, since otherwise the feed solution might enter into and displace the binding protein solution.

As discussed above, target solutes separated by the present process typically exhibit some limited solubility in both organic and aqueous phases. However, solutes separable by this hydrophilic membrane embodiment typically will be substantially more organic-soluble than water-soluble. The relative solubilities of solutes may be described in a quantitative manner by means of an aqueous-to-organic partition coefficient or solubility coefficient (S), which may be defined simply as the ratio of aqueous to organic phase solute concentrations existing at equilibrium when the mutually immiscible liquid phases are contacted. The relatively hydrophobic target solutes separable with this embodiment of the invention are characterized by relatively small values of the equilibrium partition or solubility coefficient S, e.g., about $10^5$ to about 1.0. Target solutes exhibiting partition coefficients over a very broad range will be separable by the process of the present invention.

Water-immiscible organic solvents useful for dissolving such hydrophobic solutes include but are not limited to aliphatic and aromatic hydrocarbons such as hexane and toluene; chlorinated solvents such as methylene chloride and chloroform; water-immiscible alcohols including amyl alcohol, octanol, and decanol; esters including amyl acetate; and ketones such as methyl isobutyl ketone. In choosing a solvent for this embodiment of the process, important considerations over and above its ability to dissolve the solutes of interest include its chemical compatibility with the membrane support material and with the solutes present in the feed mixture, limited aqueous-phase solubility (i.e., immiscibility with water), negligible impact on operability of the aqueous phase carrier protein, interfacial tension (as discussed further below), toxicity, viscosity, limited solubility of water within it (important to liquid membrane stability), and ability to be isolated from the solutes of interest once the primary solute separation has been effected.

In the case of chiral resolution, the feed solution presented to the separator typically will consist of a mixture of stereoisomers, one of which will be complexed preferentially by the binding protein carrier species contained within the liquid membrane. The concentration of solutes in the feed stream may vary over wide limits without affecting the performance of the present invention. Concentrations will be fixed primarily by the magnitude of the aqueous-to-organic partition or solubility coefficient S.

Once the solute has been removed from the feed mixture and selectively transported across the immobilized liquid membrane, it is recovered by its partitioning into a second water-immiscible stream, the product stream. This stream is in contact with the immobilized liquid membrane, and will frequently and preferably consist of the same water-immiscible organic solvent and in the feed stream.

The concentrations of the target and other contaminating solutes in the aqueous membrane liquid have important consequences for both the transmembrane flux as well as its selectivity. As shown below, the concentrations $C_{A1}$ and $C_{A2}$, i.e., the equilibrium concentrations of solute A at the feed (A1) and product (A2) interface will determine the optimal binding affinity for the carrier protein. Further, the solubilities of solute in the aqueous membrane liquid also determine the so-called "passive" or unfacilitated flux of both the target and other solutes across the membrane according to the solution/diffusion process described hereafter by equation (4). In order to maximize the selectivity of the membrane process, it will generally be desirable to minimize the passive diffusion component, since the latter is relatively non-selective as compared to the facilitated diffusion component which is based on the high selectivity of the synthetic binding protein. Accordingly, solvents and solutes should generally be chosen so as to minimize the aqueous solubility of the latter. In accordance with the relationship $$C_{A1},\ C_{A2} = [\text{organic-phase concentrations}] \times S$$

the solubility or partition coefficients of the solutes generally should be low in practicing this particular embodiment of the invention. When separating chemically dissimilar solutes, both chemical selectivity and partition coefficient should be considered in choosing an appropriate water-immiscible solvent. When stereoisomers are to be separated, only the magnitude of the partition coefficient will be important.

It also will be desirable to keep the concentration of the target solute in the product stream as low as possible in order to maximize the transmembrane flux. This point is discussed below with respect to equations (2), (4), and (5). Practical considerations related to product stream flow rate and recovery of dilute solute from the product stream will, in practice, dictate a lower limit for this solute concentration.

The flow rate of the product stream should be higher than that of the feed stream, typically by a ratio of at least about 1.5:1 to as high as 20:1 in order to dilute the target solute. This flow rate ratio is selected so as to result in a significant transmembrane solute concentration difference, thereby providing a sufficient driving force for the facilitated transport process.

Operating pressure is an additional important consideration because preferential wettability of the membrane support by the aqueous liquid phase cannot by itself insure adequate membrane integrity and stability. In particular, the pressure of the feed solution must be maintained within limits so as to prevent intrusion of the organic phase into the pores of the hydrophilic membrane. This maximum difference between the pressure of the organic feed stream and the aqueous membrane solution is given by the equation of Young and LaPlace, which predicts that the entry or intrusion pressure $\Delta P$ is directly proportional to the interfacial tension $\gamma$ and cosine of the contact angle $\theta$ between the organic and aqueous phases, and inversely proportional to the pore radius $R_{pore}$:

$$\Delta P = 2\gamma\cos\theta / R_{pore} \quad (1)$$

When the membrane pore size is of the order of a few tenths of a micron ($\mu$m) or smaller, the intrusion pressure is typically on the order of tens of psi. For example, the intrusion pressure predicted by equation (1) for a membrane with 0.1 $\mu$m diameter pores completely wet by an aqueous solution exhibiting an interfacial tension with an organic phase of 10 dynes/cm is approximately 44 psi. Thus, allowable feed stream operating pressures will typically be no greater than about 10 psi with such membranes and fluids in order to provide some margin of safety.

Carrier Protein

Review of the physical relationships characteristic of facilitated transport provides considerable guidance for the design of suitable synthetic binding proteins. For example, in the situation where the kinetics of both binding and release of solute by the carrier species are rapid as compared to the time for facilitated diffusion of the carrier-solute complex across the liquid membrane, the permeability P of a solute through a liquid membrane containing a carrier species capable of complexing with it is given by the equation:

$$P = SD_A(1+F) \quad (2)$$

where

S is the solubility or partition coefficient as defined above;

$D_A$ is the effective diffusivity of solute A in the membrane; and

F is the facilitation factor.

The transmembrane flux J of solute varies in direct proportion to the permeability and solute concentration difference $\Delta C$ across it, and inversely with the membrane thickness L, as indicated below:

$$J = P\Delta C/L \quad (3)$$

Other factors such as process-stream boundary layer resistances to diffusion also may affect the transmembrane flux, but have little influence on binding protein design, are not unique to the present invention, and are well understood by those skilled in the art.

The effective diffusivities ($D_i$) of both "free" solute as well as that of the protein/solute complex in the immobilized liquid membrane depend on both solution and membrane properties. Thus:

$$D_i = D_o\,\epsilon/\tau \quad (4)$$

where $D_o$ is the free solution diffusivity of species "i", $\epsilon$ is the membrane porosity, and $\tau$ is the membrane tortuosity (i.e., the ratio of the diffusion path length to membrane thickness). High porosity and low tortuosity are desirable membrane characteristics. Typically, membranes useful in the practice of the invention will exhibit porosities in the range of 50 to 95%, and tortuosity factors of from about 1.1 to 4.

The facilitation factor F expresses the extent to which carrier-mediated transport increases the selective permeation flux over and above simple passive diffusion $D_p$ as given by the equation:

$$D_p = SD_A \quad (5)$$

For the case of rapid reaction kinetics, the facilitation factor is given by the equation:

$$F = (D_{CA}/D_A)KC_T/[(1+KC_{A1})(1+KC_{A2})] \quad (6)$$

where $D_{CA}$ is the effective diffusivity of the solute/carrier complex in the liquid membrane;

K is the equilibrium binding constant describing the association between carrier and solute, and equals the quotient of the on and off rate constants, $K_1/K_2$;

$C_T$ is the solubility of carrier (in both its "free" and complexed forms) in the liquid membrane;

$C_{A1}$ is the concentration of solute in the liquid at that surface of the membrane in contact with the feed stream; (interface 56, FIG. 1); and $C_{A2}$ is the (lower) concentration of solute in the liquid at that surface of the membrane in contact with the product stream (interface 58, FIG. 1).

From the foregoing and other equations provided below, it is possible to specify the particular physical, and chemical properties of synthetic binding proteins, solutes, and organic solvents that optimize the process of the present invention. Further, it is possible to understand why use of synthetic binding proteins in combination with facilitated-transport in immobilized liquid membranes is especially powerful.

For example, as regards the desired physical properties of the binding protein, it is clear from equation (6) that the degree of facilitation (as expressed by the facilitation factor F) is maximized by large values of the effective diffusivity of the carrier/solute complex as well as that of the free solute, and by high concentrations of the carrier species $C_T$. The facilitated diffusion flux is proportional to the maximum molar concentration of the carrier protein in the fixed intrapore space of a liquid membrane. Given similar solubilities in weight concentration (mg/ml) for different carrier molecules, the lowest molecular weight species will have the highest molar concentration and hence the largest number of carrier molecules in the liquid membrane. This consideration makes engineered binding proteins (as opposed to native forms such as monoclonal antibodies and natural receptors) particularly attractive in facilitated transport processes, since such engineered proteins can exhibit the binding specificity and avidity of native binding proteins at a fraction of their molecular weight. More particularly, whereas antibodies of the IgG class are characterized by molecular weights of order 150,000 daltons, it is now possible to produce synthetic proteins with molecular weights that are nearly ten-fold smaller. At present, biosynthetic binding sites with excellent binding properties are available with water solubilities at least as high as about 5 mg/mL or about 0.0002 M.

Additionally, the ability to genetically engineer ancillary domains onto synthetic binding proteins in addition to the binding domain can improve further their solubility in a given solvent and reduce tendency toward aggregation.

The relatively low molecular weight characteristic of synthetic binding proteins favors not only high solubility but also higher diffusivity, making carrier-mediated membrane transport processes significantly more efficient. However, it should be noted that high carrier protein concentrations also can have the effect of increasing viscosity, and diffusivity typically varies inversely with solution viscosity.

Ideally, the kinetics of both protein/solute binding (i.e., the "on" rate) and of protein/solute dissociation (i.e., the "off" rate) should be large, i.e., both the second-order rate constant $k_2$ describing the "on" rate and the first-order rate constant $k_1$ describing the "off" rate should be large. These are related through the affinity of the binding protein, with the ratio of "on" and "off" rate constants $k_2/k_1$ being equal to the protein binding constant K. If these reaction rates are slow as compared to the rate of diffusion of the protein/solute complex across the liquid membrane, then the facilitated transport process will be kinetically controlled. In this event the transmembrane flux and the selectivity of the separation are still achieved but can be significantly lower than predicted by the above equations.

One semi-quantitative approach for estimating the significance of binding and release kinetics to the performance of such carrier mediated transport involves calculating a dimensionless Damkohler number (D) which compares a characteristic reaction time ($T_r$) with a characteristic transmembrane diffusion time ($T_d$) as follows:

$$D = T_r/T_d \quad (7)$$

where $$T_r = 1/(k_2 * C_T) \text{ (for the binding reaction)} \quad (8)$$

$$T_r 1/k_1 \text{ (for solute release), and} \quad (9)$$

$$T_d = L^2/Di \quad (10)$$

For small values of the Damkohler number as defined above for both the forward (or "on") and reverse (or "off") reactions, reaction kinetics will not be limiting, and permeation rates will be diffusion-controlled.

Synthetic binding proteins useful in the present invention typically will be characterized by rate constants for the association reaction of order $5\times10^5$ to $6\times10^8$ liters per mole-sec, although higher and lower values are possible. Reasonable estimates of the Damkohler number corresponding to these binding kinetics range from about $10^{-8}$ to $10^{-3}$, suggesting that "on" rates will not be a significant limiting factor. Dissociation rate constants might vary from about 0.1 to about 6000 inverse seconds, with the corresponding Damkohler numbers ranging from about $10^{-6}$ to about 1. Thus, synthetic binding proteins can be designed and/or selected by this criterion for which neither binding nor release kinetics are limiting. The above calculation clearly indicates that finite "off" rates will generally be of greater concern than "on" rates. A significant advantage of the novel synthetic binding proteins exploited in preferred embodiments of the present invention is the ability independently to manipulate and select for a binding protein with an optimum combination of binding equilibrium constant K and association/dissociation rate constants $k_2$ and $k_1$, as discussed below.

The Binding Protein

While conventional monoclonal antibodies can be used in the process and apparatus of the invention, from the foregoing it will be apparent that their high molecular weight and large size make such proteins less than optimal. Fortunately the art of producing chimeric antibodies missing all or part of the constant region, FVs, FV' dimers, and other such constructs is well developed. See, for example, U.S. Pat. No. 4,816,567 and U.S. Pat. No. 4,642,334. However, the currently preferred methods for making biosynthetic antibody binding sites (BABS), for altering their affinity and specificity by cassette mutagenesis, and for tailoring their solubility properties are disclosed in copending U.S. application Ser. No. 052,800 filed May 21, 1987, U.S. Ser. No. 342,449 filed Feb. 6, 1989, and in published PCT Application US88/01737, the disclosures of which are herein incorporated by reference.

These biosynthetic polypeptides define structure capable of selective antigen recognition and preferential antigen binding, and preferably also one or more peptide-bonded additional protein or polypeptide regions or domains designed to have a preselected property. For the practice of this invention, the second region or domain may be entirely eliminated, or may be included to influence the solubility properties of the binding protein for the liquid phase in either the immobilized liquid membrane or solvent extraction embodiments.

This technology provides intact biosynthetic antibody binding sites analogous to $V_H$-$V_L$ dimers, either non-covalently associated, disulfide bonded, or preferably linked by a polypeptide sequence to form a composite $V_H$-$V_L$ or $V_L$-$V_H$ polypeptide which may be essentially free of antibody constant region. The technology also provides proteins analogous to an independent $V_H$ or $V_L$ domain, dimers thereof or single chain dimers. Any of these proteins may be provided in a form linked to, for example, amino acids designed to promote water solubility, or solubility in organic solvents, as the case may be.

The design of the BABS is based on the observation that the variable domains of each of the heavy and light chains of native immunoglobulin molecules collectively are responsible for antigen recognition and binding. Each of these domains contain subregions, called "complementarity determining regions" or CDRs, consisting of one of the hypervariable regions or loops and of selected amino acids or amino acid sequences disposed in the framework regions (FRs) which flank that particular hypervariable region. Biosynthetic domains mimicking the structure of the two chains of an immunoglobulin binding site may be connected by a polypeptide linker while closely approaching, retaining, and often improving their collective binding properties.

As is now well known, Fv, the minimum antibody fragment which contains a complete antigen recognition and binding site, consists of a dimer of one heavy and one light chain variable domain in noncovalent association. It is in this configuration that the three complementarity determining regions of each variable domain interact to define an antigen binding site on the surface of the $V_H$-$V_L$ dimer. Collectively, the six complementarity determining regions (see FIG. 3) confer antigen binding specificity to the antibody. FRs flanking the CDRs have a tertiary structure which is essentially conserved in native immunoglobulins. These FRs serve to hold the CDRs in their appropriate orientation. The constant domains are not required for binding function. Even a single variable domain (or half of an Fv comprising only three CDRs specific for an antigen) has the ability to recognize and bind antigen, although at a lower affinity than an entire binding site (Painter et al. (1972) Biochem. 11:1327-1337), and may be used as carrier proteins.

The term CDR, as used herein, refers to amino acid sequences which together define the binding affinity and specificity of the natural Fv region of a native immunoglobulin binding site, or a synthetic polypeptide which mimics this function. CDRs typically are not wholly homologous to hypervariable regions of natural Fvs, but rather also may include specific amino acids or amino acid sequences which flank the hypervariable region and have heretofore been considered framework not directly determinitive of complementarity. The term FR, as used herein, refers to amino acid sequences flanking or interposed between CDRs. The CDR and FR polypeptide segments are designed based on sequence analysis of the Fv region of preexisting antibodies or of the DNA encoding them.

The binding site region of BABS constructs comprises at least one, and preferably two domains, each of which have amino acid sequences homologous to portions of the CDRs of the variable domain of an immunoglobulin light or heavy chain, and other sequences homologous to the FRs of the variable domain. The two domain binding site construct also includes a polypeptide linking the domains. Polypeptides so constructed bind a specific preselected antigen determined by the CDRs held in proper conformation by the FRs and the linker. Preferred structures have linked domains which together comprise structure mimicking a $V_H$-$V_L$ or $V_L$-$V_H$ immunoglobulin two-chain binding site. CDR regions of a mammalian immunoglobulin, such as those of mouse or rat are preferred, and typically are copies or patterned after a monoclonal antibody. In addition, the chimeric polypeptide may comprise other amino acid sequences. It may comprise, for example, a sequence homologous to a portion of the constant domain of an immunoglobulin, but preferably is free of constant regions (other than FRs).

The binding site region(s) of the chimeric proteins are thus single chain composite polypeptides comprising a structure which in solution behaves like an antibody binding site. The two domain, single chain composite polypeptide has a structure patterned after tandem $V_H$ and $V_L$ domains, but with the carboxyl terminus of one attached through a linking amino acid sequence to the amino terminus of the other. The linker preferably spans a distance of at least about 40Å, i.e., comprises at least about 14 amino acids, and comprises residues which together present a hydrophilic, relatively unstructured region. Linking amino acid sequences having little or no secondary structure work well.

Either the amino or carboxyl terminal ends (or both ends) of these chimeric, single chain binding sites may be attached to an amino acid sequence which has the function of increasing solubility in the liquid phase of the immobilized liquid membrane or solvent extraction apparatus. Because such structures are designed at the DNA level, specificities and affinity can be varied by cassette mutagenesis as disclosed herein and in U.S. Pat. No. 4,888,286 to optimize utility in the separation process. The synthetic proteins can be expressed in procaryotes such as *E. coli* and thus are less costly to produce than immunoglobulins or fragments thereof which require expression in cultured animal cell lines.

FIGS. 7A-7D illustrate four examples of protein structures that can be produced by following the teaching disclosed herein and in the aforementioned patent documents. All are characterized by a biosynthetic polypeptide defining a binding site 3, comprising amino acid sequences comprising CDRs and FRs, often derived from different immunoglobulins, or sequences homologous to a portion of CDRs and FRs from different immunoglobulins. FIG. 7A depicts a single chain construct comprising a polypeptide domain 10 having an amino acid sequence analogous to the variable region of an immunoglobulin heavy chain, bound through its carboxyl end to a polypeptide linker 12, which in turn is bound to a polypeptide domain 14 having an amino acid sequence analogous to the variable region of an immunoglobulin light chain. Of course, the light and heavy chain domains may be in reverse order. Alternatively, the binding site may comprise two substantially homologous amino acid sequences which are both analogous to the variable region of an immunoglobulin heavy or light chain.

The linker 12 should be long enough (e.g., about 15 amino acids or about 40 Å) to permit the chains 10 and 14 to assume their proper conformation. The linker preferably comprises hydrophilic amino acid sequences. The amino acids of the linker preferably are selected from among those having relatively small, unreactive side chains. Alanine, serine, and glycine are preferred. Generally, the properties of the linked domains are seriously degraded if the linker sequence is shorter than about 35Å in length, i.e., comprises less than about 10 residues. Linkers longer than the approximate 40Å distance between the N terminal of a native variable region and the C-terminal of its sister chain may be used, but also potentially can diminish the BABS binding properties. Linkers comprising between 12 and 18 residues are preferred. The preferred length in specific constructs may be determined by varying linker length first by units of 5 residues, and second by units of 1-4 residues after determining the best multiple of the pentameric starting units.

Figure 7C:
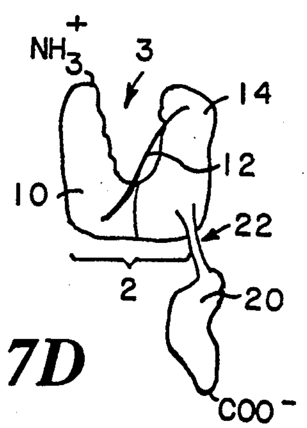
Figure 7D:
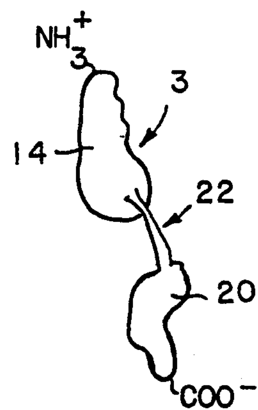

Additional proteins or polypeptides may be attached to either or both the amino or carboxyl termini of the binding site to influence solubility and to produce proteins of the type illustrated in FIGS. 7B-7D. As an example, in FIG. 7B, a helically coiled polypeptide structure 16 comprises a protein A fragment (FB) linked to the amino terminal end of a $V_H$-like domain 10 via a spacer sequence 18. The FB domain 16 has the effect of enhancing water solubility. FIG. 7C illustrates a protein having a solubility enhancing polypeptide 20 linked via a spacer sequence 22 to the carboxyl terminus of polypeptide 14 of binding protein segment 2.

The domains are attached by a spacer 18 (FIGS. 7B) covalently linking the C terminus of the protein 16 to the N-terminus of the first domain 10 of the binding protein segment 2, or by a spacer 22 linking the C-terminus of the second binding domain 14 to the N-terminus of another protein (FIGS. 7C and 7D). The spacer may be an amino acid sequence analogous to linker sequence 12, or it may take other forms.

FIG. 7D depicts another type of reagent, comprising a BABS having only one set of three CDRs, e.g., analogous to a heavy chain variable region, which retains a measure of affinity for the antigen. Attached to the carboxyl end of the polypeptide 10 or 14 comprising the FR and CDR sequences constituting the binding site 3 through spacer 22 is solubility enhancing polypeptide 20 as described above.

Design and Manufacture

The binding proteins are designed at the DNA level. A preferred general structure of the DNA encoding the proteins encodes an optional leader sequence used to promote expression in procaryotes having a built-in cleavage site recognizable by a site specific cleavage agent, for example, an endopeptidase, used to remove the leader after expression. This is followed by DNA encoding a $V_H$-like domain, comprising CDRs and FRs, a linker, a $V_L$-like domain, again comprising CDRs and FRs, and an optional second domain for solubility enhancement. This region of the DNA may encode, for example Gly, Ala, Ser, Thr, Asp, Glu, Lys, Arg, and/or His in various sequences of various lengths to impart hydrophilic character and to promote water solubility. The chimeric or synthetic DNAs are then expressed in a suitable host system, and the expressed proteins are collected and renatured if necessary. After expression, folding, and cleavage of the leader, a protein results having a binding region whose specificity is determined by the CDRs.

The ability to design BABS useful in the invention depends on the ability to determine the sequence of the amino acids in the variable region of monoclonal antibodies of interest, or the DNA encoding them. Hybridoma technology enables production of cell lines secreting antibody to essentially any desired substance that produces an immune response. RNA encoding the light and heavy chains of the immunoglobulin can then be obtained from the cytoplasm of the hybridoma. The 5′ end portion of the mRNA can be used to prepare cDNA that permits V gene cloning and subsequent sequencing, or the amino acid sequence of the hypervariable and flanking framework regions can be determined by amino acid sequencing of the V region fragments of the H and L chains. Such DNA sequence analysis is now conducted routinely and rapidly. This knowledge, coupled with observations and deductions of the generalized structure of immunoglobulin Fvs, permits one to design synthetic genes encoding FR and CDR sequences which likely will bind the antigen. These synthetic genes are then prepared using known techniques, or using the technique disclosed below, inserted into a suitable host, and expressed, and the expressed protein is purified. Depending on the host cell, renaturation techniques may be required to attain proper conformation. The various proteins are then tested for binding ability, and one having appropriate affinity is selected for incorporation into a system of the type described above. If necessary, point substitutions seeking to optimize binding properties may be made in the DNA using conventional cassette mutagenesis.

It typically will be desirable that the specificity of binding of a particular target solute by the BABS protein be made as high as possible by techniques described herein. However, as can be seen from equation (6), the facilitation factor depends in a complex manner on the equilibrium binding constant K, which is defined as follows:

$$K = [\textit{protein/solute complex}]/[\textit{protein}][\textit{solute}] \quad (11)$$

By taking the first derivative of the facilitation factor F with respect to the binding constant K in equation (6) and setting the result to zero, an optimum value of the binding constant K may be calculated that maximizes the facilitation-diffusion flux of solute across the membrane. This optimum value for K is given simply as the reciprocal of the geometric mean of the "feed-side" and "product-side" membrane-phase solute concentrations as shown below:

$$K\,(\text{optimum}) = 1/(C_{A1} \times C_{A2})^{0.5} \quad (12)$$

where the two concentrations have been described above. The lower these solute concentrations, the higher will be the optimum affinity. These concentrations will depend on feed concentrations, product-to-feed stream flowrate ratios, and partition coefficients, (solvent selections), as discussed previously.

Accordingly, it can be seen that there exists an optimum affinity between the BABS carrier protein and the solute, and that the optimum value will depend on process conditions related to solute concentrations at the membrane interfaces. Values of K significantly much higher than this optimum value will result in "saturation" of the facilitated transport process and poor release of the transported solute from the carrier/solute complex. On the other hand, values of K significantly much lower than this optimum value will result in formation of only small concentrations of the complex between solute and BABS carrier protein, with the result that little carrier-mediated facilitation will take place.

Ideally, the synthetic binding protein will exhibit an affinity or equilibrium binding constant K which is within at least about an order of magnitude of the optimum binding constant as given by equation (12) above. Preferred affinities or binding constants will typically be in the range from about $10^3$ to about $10^9$ liters per mole, the precise optimal value depending on solute concentrations as discussed above. An important advantage of synthetic binding proteins in these membrane separation applications is the ability to vary the protein/solute affinity in a rational manner so as to maximize the efficiency of the membrane separation processes. Affinity constants can be reduced easily by amino acid substitution in the CDR regions of the binding site. Accordingly, one strategy is to select a high affinity mononclonal, and then to reduce its affinity by site directed cassette mutagenesis to an appropriate level as dictated by the foregoing parameters.

The construction of DNAs encoding proteins as disclosed herein can be done using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic probes for isolating immunoglobulin or other bioactive protein genes. Various promoter sequences and other regulatory DNA sequences used in achieving expression, and various types of host cells are also known and available. Conventional transfection techniques, and equally conventional techniques for cloning and subcloning DNA are useful in the manufacture of proteins of the type disclosed herein and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector. One preferred method for obtaining DNA encoding the proteins disclosed herein is by assembly of synthetic oligonucleotides produced in a conventional, automated, polynucleotide synthesizer followed by ligation with appropriate ligases.

A method of producing the BABS of the invention is to produce a synthetic DNA encoding a polypeptide comprising FRs and intervening "dummy" CDRs, or amino acids having no function except to define suitably situated unique restriction sites. This synthetic DNA is then altered by DNA replacement, in which restriction and ligation is employed to insert synthetic oligonucleotides encoding CDRs defining a desired binding specificity in the proper location between the FRs. This approach facilitates empirical refinement of the binding properties of the BABS.

This technique is dependent upon the ability to cleave a DNA corresponding in structure to a variable domain gene at specific sites flanking nucleotide sequences encoding CDRs. These restriction sites in some cases may be found in the native gene. Alternatively, non-native restriction sites may be engineered into the nucleotide sequence resulting in a synthetic gene with a different sequence of nucleotides than the native gene, but encoding the same variable region amino acids because of the degeneracy of the genetic code. The fragments resulting from endonuclease digestion, and comprising FR-encoding sequences, are then ligated to non-native CDR-encoding sequences to produce a synthetic variable domain gene with altered antigen binding specificity.

FIG. 4 discloses the nucleotide and corresponding amino acid sequence (shown in standard single letter code) of a synthetic DNA comprising a master framework gene having the generic structure:

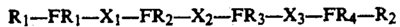

$$R_1—FR_1—X_1—FR_2—X_2—FR_3—X_3—FR_4—R_2$$

where $R_1$ and $R_2$ are restricted ends which are to be ligated into a vector, and $X_1$, $X_2$, and $X_3$ are DNA sequences whose function is to provide convenient restriction sites for CDR insertion. This particular DNA has murine FR sequences and unique, 6-base restriction sites adjacent the FR borders so that nucleotide sequences encoding CDRs from a desired monoclonal can be inserted easily. Restriction endonuclease digestion sites are indicated with their abbreviations; enzymes of choice for CDR replacement are underscored. Digestion of the gene with the following restriction endonucleases results in 3' and 5' ends which can easily be matched up with and ligated to native or synthetic CDRs of desired specificity; KpnI and BstXI are used for ligation of $CDR_1$; XbaI and DraI for $CDR_2$; and BssHII and ClaI for $CDR_3$.

The expression of these synthetic DNA's can be achieved in both prokaryotic and eucaryotic systems via transfection with an appropriate vector. In *E. coli* and other microbial hosts, the synthetic genes can be expressed as fusion protein which is subsequently cleaved. Expression in eucaryotes can be accomplished by the transfection of DNA sequences encoding CDR and FR region amino acids into a myeloma or other type of cell line. By this strategy intact hybrid Fv regions may be produced.

Exemplary Design of Synthetic $V_H$ and $V_L$ Mimics

A synthetic protein consisting of the FB fragment of protein A as a leader coupled to a single chain binding site comprising the variable regions of the light and heavy chains of monoclonal 26-10 was designed at the DNA level, expressed, purified, renatured, shown to bind specifically with the preselected antigen (digoxin), and shown to act as a protein binding site in the process of the invention. The detailed primary structure of this construct is shown in FIG. 6; its tertiary structure is illustrated schematically in FIG. 7B.

GENE DESIGN

Given known variable region DNA sequences, synthetic $V_L$ and $V_H$ genes may be designed which encode native or near native FR and CDR amino acid sequences from an antibody molecule, each separated by unique restriction sites located as close to FR-CDR and CDR-FR borders as possible. Alternatively, genes may be designed which encode native FR sequences which are similar or identical to the FRs of an antibody molecule from a selected species, each separated by "dummy" CDR sequences as discussed above. These DNAs serve as starting materials for producing BABS, as the native or "dummy" CDR sequences may be excised and replaced with sequences encoding the CDR amino acids defining a selected binding site. Any one of the $V_H$ and $V_L$ sequences described above may be linked together via an amino acid linker connecting the C-terminus of one chain with the N-terminus of the other.

These genes, once synthesized, may be cloned with or without additional DNA sequences coding for a leader peptide which facilitates secretion or the solubility of the fusion polypeptide. The genes then can be expressed directly in an appropriate host cell, or can be further engineered before expression by the exchange of FR, CDR, or "dummy" CDR sequences with new sequences. This manipulation is facilitated by the presence of the restriction sites which have been engineered into the gene at the FR-CDR and CDR-FR borders. Significant flexibility in $V_H$ and $V_L$ design is possible because the amino acid sequences are determined at the DNA level, and the manipulation of DNA can be accomplished easily.

By sequencing any antibody, or obtaining the sequence from the literature, in view of this disclosure one skilled in the art can produce a BABS of any desired specificity comprising any desired framework region. Diagrams comparing the amino acid sequence of different V genes are valuable in suggesting which particular amino acids should be replaced to determine the desired complementarity. Expressed sequences may be tested for binding and refined by exchanging selected amino acids in relatively conserved regions, based on observation of trends in amino acid sequence data and/or computer modeling techniques.

For example, the DNA sequence for murine $V_H$ and $V_L$ 26-10 containing specific restriction sites flanking each of the three CDRs was designed with the aid of a commercially available computer program which performs combined reverse translation and restriction site searches ("RV.exe" by Compugene, Inc.). The known amino acid sequences for $V_H$ and $V_L$ 26-10 polypeptides were entered, and all potential DNA sequences which encode those peptides and all potential restriction sites were analyzed by the program. The program can, in addition, select DNA sequences encoding the peptide using only codons preferred by *E. coli* if this bacterium is to be host expression organism of choice.

The DNA sequences for the synthetic 26-10 $V_H$ and $V_L$ are designed so that one or both of the restriction sites flanking each of the three CDRs are unique. A six base site (such as that recognized by Bsm I or BspM I) is preferred, but where six base sites are not possible, four or five base sites are used. These sites, if not already unique, are rendered unique within the gene by eliminating other occurrences within the gene without altering necessary amino acid sequences. Preferred cleavage sites are those that, once cleaved, yield fragments with sticky ends just outside of the boundary of the CDR within the framework. However, such ideal sites are only occasionally possible because the FR-CDR boundary is not an absolute one, and because the amino acid sequence of the FR may not permit a restriction site. In these cases, flanking sites in the FR which are more distant from the predicted boundary are selected.

EXPRESSION OF PROTEINS

The engineered genes can be expressed in appropriate prokaryotic hosts such as various strains of *E. coli.* and in eucaryotic hosts such as Chinese hamster ovary cell, murine myeloma, and human myeloma/transfectoma cells.

For example, if the gene is to be expressed in *E. coli,* it may first be cloned into an expression vector. This is accomplished by positioning the engineered gene downstream from a promoter sequence such as trp or tac, and a gene coding for a leader peptide. The resulting expressed fusion protein accumulates in refractile bodies in the cytoplasm of the cells, and may be harvested after disruption of the cells by French press or sonication. The refractile bodies are solubilized, and the expressed proteins refolded and cleaved by the methods already established for many other recombinant proteins.

If the engineered gene is to be expressed in myeloma cells, the conventional expression system for immunoglobulins, it is first inserted into an expression vector containing, for example, the Ig promoter, a secretion signal, immunoglobulin enhancers, and various introns. This plasmid may also contain sequences encoding all or part of a constant region, enabling an entire part of a heavy or light chain to be expressed. The gene is transfected into myeloma cells via established electroporation or protoplast fusion methods. Cells so transfected can express $V_L$ or $V_H$ domains, $V_{L2}$ or $V_{H2}$ homodimers, $V_L$-$V_H$ heterodimers, $V_H$-$V_L$, $V_L$-$V_H$, $V_L$-$V_L$, or $V_H$-$V_H$ single chain polypeptides, complete heavy or light immunoglobulin chains, or portions thereof, each of which optionally may be attached in the various ways discussed above to a pendant protein which promote solubility.

Vectors containing a heavy chain V region (or V and C regions) can be cotransfected with analogous vectors carrying a light chain V region (or V and C regions), allowing for the expression of noncovalently associated binding sites (or complete antibody molecules).

Hydrophobic Liquid Membrane Supports

Given the above teaching of the embodiment of the invention for the case of preferentially organic-soluble solutes, hydrophilic support membranes, and water-soluble synthetic binding proteins, the operation of the invention for the case where the target solute exhibits high water solubility (i.e., high aqueous-to-organic partition or solubility coefficient S) should be readily apparent. In this situation, the support membrane should be hydrophobic and the binding protein should be soluble and active in organic solvents (e.g., those recited above as suitable feed and product-stream diluents). In this case it will be important to engineer into the binding proteins stability in the chosen organic solvent and a hydrophobic leader or tail which functions analogously to the hydrophobic region of biological transmembrane receptors and is rich in hydrophobic amino acids such as phenylananine, leucine, alanine, tryptophan, and proline, and may also contain isoleucine, valine, and methionine. In this region, hydrophilic amino acids such as glutamic or aspartic acid, lysine, arginine, and the like should be avoided or their use should be restricted.

Organic solutions of synthetic binding proteins can be employed as liquids in hydrophobic membrane structures in a manner entirely analogous to that described above, with the exception that the membrane polymer is "wet" by the organic phase. Suitable hydrophobic membrane polymers include but are not limited to polytetrafluoroethylene, polyvinylchloride, and other polyolefins including polyethylene and polypropylene.

In most respects, the design considerations and operating parameters pertinent to this embodiment of the invention parallel precisely those described above for the hydrophilic former embodiment. Basic operating principles are identical, and the identical design equations apply. However, because the feed and process streams are aqueous, such parameters as the pH and/or concentration of salt in the aqueous feed and product streams can be manipulated independently. In particular, it will be possible to control the feed stream pH and/or salt concentration at values that favor the binding of target solute to the synthetic binding protein while, at the same time, maintaining the pH and/or salt concentration of the product stream at values that favor dissociation of the protein/solute complex. When the process is operated in this manner, there does not exist an "optimum" value for the binding constant K which is analogous to that predicted for the previous embodiment by equation (12). Rather, it is the sensitivity of K to variations in pH, salt concentration, or some additional solution parameter that becomes important to the design and operation of the membrane process.

Membrane Solvent Extraction

This embodiment of the invention is closely related to the above-described process of facilitated transport in immobilized liquid membranes. However, as noted above with respect to the description of FIG. 2, it is based on circulating a solution of synthetic binding protein between two membrane separators by convection using a pump or the like.

In one embodiment of this membrane-mediated extraction process, an organic-phase feed stream containing a mixture of solutes is contacted with an aqueous solution of synthetic binding protein across a microporous membrane 52 (either hydrophilic or hydrophobic). Selective transfer of solute across the phase-separating membrane 52 and attendant complexation with the binding protein in the circulating aqueous solution occur in this "extractor" or "absorber" unit, with the solute-rich aqueous solution subsequently being pumped to a second membrane 52' where contact between the circulating aqueous solution and the product stream takes place. Dissociation of complex and transfer of solute across the membrane 52' are thus made to occur in this second "back-extractor" or "desorber" unit (See FIG. 2) The resulting solute-lean aqueous solution of synthetic binding protein is then recirculated to the membrane absorber to complete the process cycle.

The essential principles of design and operation of this embodiment of the invention closely parallel those for facilitated-transport immobilized liquid membranes discussed above. The principal exception is that the productivity of the process is determined not only by the rates of solute uptake in and release by the carrier protein in the absorber and desorber, but by this parameter in conjunction with the rate of circulation between the two membrane phase separators. Solute transfer between aqueous and organic phases in the absorber and desorber individually will be determined by processes of transmembrane and boundary layer diffusion and the intrinsic kinetics of solute binding and release by the synthetic binding protein substantially as described above. In effect, the process of transmembrane diffusion of a solute/protein complex between the two surfaces of a single immobilized liquid membrane in simultaneous contact with two process streams is simply replaced by a process wherein convective transport of binding protein and its solute complex takes place between two membrane separators, each of which contacts the absorbent solution with a single immiscible process stream.

As with immobilized liquid membranes, it will be important to operate this embodiment within certain pressure ranges in order to maintain successfully a stable aqueous/organic interface in the two membrane separators. For example, if the membrane is hydrophilic and therefore wet with the circulating aqueous solution of synthetic binding protein, it will be desirable to maintain a small positive pressure difference across the membrane (e.g., by means of a back-pressure regulator or some other pressure control device), with the organic phase (i.e., the feed or product stream) being held at the greater pressure.

When operated in this manner, the aqueous/organic phase boundary will be located at the surface of the membrane in contact with the organic process stream, and this location will be a stable one. Ultrafiltration of aqueous solution across the membrane will be prevented by the opposing pressure difference (i.e., organic-to-aqueous), but the hydrophilicity of the membrane will ensure that the membrane is preferentially wet by the aqueous phase. The principal restriction on the magnitude of the organic-to-aqueous pressure difference (other than the requirement that the membrane possess adequate mechanical strength) is that the pressure not exceed the intrusion pressure for penetration of membrane pores by the non-wetting organic phase. The intrusion pressure can be determined from the equation of Young and LaPlace as discussed above.

It frequently will be preferable from a mass transfer viewpoint to employ hydrophobic membranes as phase separators with aqueous solutions of synthetic binding proteins. While the invention is operable using either type of membrane, transport rates typically will be higher if the design avoids the necessity for the protein/solute carrier to diffuse across the phase-separating membranes. This is the case when an aqueous solution of binding protein is used with a hydrophilic membrane.

It will further be apparent that this embodiment also is operable in the case of preferentially water-soluble solutes and circulating organic-phase solutions of synthetic binding proteins. As with the analogous liquid membrane process, the additional degree of freedom represented by the ability independently to vary aqueous feed-and-product stream solution parameters such as pH and salt concentration may be used to advantage in this event to modulate the affinity of the synthetic binding protein for the target solute and so improve the efficiency of turnover of said binding protein.

The invention will be further understood from the following, non limiting examples.

EXAMPLE 1

This example demonstrates facilitated transport of the cardiac glycoside oleandrin, an analog of digoxin, through a supported liquid membrane using the biosynthetic binding protein FB-sFv 26-10, made as described below.

Production of BABS for Digoxin-like Cardiac Glycosides

The digoxin binding site of the $IgG_{2a,k}$ monoclonal antibody 26-10 has been analyzed by Mudgett-Hunter and colleagues. The 26-10 V region sequences were determined from both amino acid sequencing and DNA sequencing of 26-10 H and L chain mRNA transcripts (D. Panka, J. Novotny, and M.N. Margolies, unpublished data). The 26-10 antibody exhibits a high digoxin binding affinity [$K_o = 5.4 \times 10^9 M^{-1}$] and has a well-defined profile of specificity to various digoxin analogs including oleandrin. This provided a baseline for comparison between the monoclonal and the biosynthetic binding sites mimicking its structure.

Protein Design:

Crystallographically determined atomic coordinates for Fab fragments of 26-10 were obtained from the Brookhaven Data Bank. Inspection of the available three-dimensional structures of Fv regions within their parent Fab fragments indicated that the Euclidean distance between the C-terminus of the $V_H$ domain and the N-terminus of the $V_L$ domain is about 35 Å. Considering that the peptide unit length is approximately 3.8 Å, a 15 residue linker was selected to bridge this gap. The linker was designed so as to exhibit little propensity for secondary structure and not to interfere with domain folding. Thus, the 15 residue sequence $(Gly\text{-}Gly\text{-}Gly\text{-}Gly\text{-}Ser)_3$ was selected to connect the $V_H$ carboxyl and $V_L$ amino termini.

Binding studies with single chain binding sites having less than or greater than 15 residues demonstrate the importance of the prerequisite distance which must separate $V_H$ from $V_L$; for example, a $(Gly_4\text{-}Ser)_1$ linker does not demonstrate binding activity, and those with $(Gly_4\text{-}Ser)_5$ linkers exhibit lower activity compared to those with $(Gly_4\text{-}Ser)_3$ linkers.

Gene Synthesis:

Design of the 744 base sequence for the synthetic binding site gene was derived from the Fv protein sequence of 26–10 by choosing codons frequently used in *E. coli*. Synthetic genes coding or the trp promoter-operator, the modified trp LE leader peptide (MLE), the sequence of which is shown in FIG. 9, and $V_H$ were prepared generally as described above. The gene coding for $V_H$ was assembled from 46 chemically synthesized oligonucleotides, all 15 bases long, except for terminal fragments (13 to 19 bases) that included cohesive cloning ends. Between 8 and 15 overlapping oligonucleotides were enzymatically ligated into double stranded DNA, cut at restriction sites suitable for cloning (NarI, XbaI, SalI, SacII, SacI), purified by PAGE on 8% gels, and cloned in pUC which was modified to contain additional cloning sites in the polylinker. The cloned segments were assembled stepwise into the complete gene mimicking $V_H$ by ligations in the pUC cloning vector.

The gene mimicking 26–10 $V_L$ was assembled from 12 long synthetic polynucleotides ranging in size from 33 to 88 base pairs, prepared in automated DNA synthesizers (Model 6500, Biosearch, San Rafael, Calif.; Model 380A, Applied Biosystems, Foster City, Calif.). Five individual double stranded segments were made out of pairs of long synthetic oligonucleotides spanning six-base restriction sites in the gene (AatII, BstEII, PpnI, HindIII, BglII, and PstI). In one case, four long overlapping strands were combined and cloned. Gene fragments bounded by restriction sites for assembly that were absent from the pUC polylinker, such as AatII and BstEII, were flanked by EcoRI and BamHI ends to facilitate cloning.

The linker between $V_H$ and $V_L$, encoding $(Gly\text{-}Gly\text{-}Gly\text{-}Gly\text{-}Ser)_3$, was cloned from two long synthetic oligonucleotides, 54 and 62 bases long, spanning SacI and AatII sites, the latter followed by an EcoRI cloning end. The complete single chain binding site gene was assembled from the $V_H$, $V_L$, and linker genes to produce a construct, corresponding to aspartyl-prolyl-$V_H$-<linker>-$V_L$, flanked by EcoRI and PstI restriction sites.

The trp promoter-operator, starting from its SspI site, was assembled from 12 overlapping 15 base oligomers, and the MLE leader gene was assembled from 24 overlapping 15 base oligomers. These were cloned and assembled in pUC using the strategy of assembly sites flanked by cloning sites. The final expression plasmid was constructed in the pBR322 vector by a 3-part ligation using the sites SspI, EcoRI, and PstI (see FIG. 10B). Intermediate DNA fragments and assembled genes were sequenced by the dideoxy method.

Fusion Protein Expression:

Single-chain protein was expressed as a fusion protein. The MLE leader gene (FIG. 10) was derived from *E. coli* trp LE sequence and expressed under the control of a synthetic trp promoter and operator. *E. coli* strain JM83 was transformed with the expression plasmid and protein expression was induced in M9 minimal medium by addition of indoleacrylic acid (10 mg/ml) at a cell density with $A_{600}=3$. The high expression levels of the fusion protein resulted in its accumulation as insoluble protein granules, which were harvested from cell paste.

Fusion Protein Cleavage:

The MLE leader was removed from the binding site protein by acid cleavage of the Asp-Pro peptide bond engineered at the junction of the MLE and binding site sequences. The washed protein granules containing the fusion protein were cleaved in 6 M guanidine-HCl+10% acetic acid, pH 2.5, incubated at 37° C. for 96 hrs. The reaction was stopped through precipitation by addition of a 10-fold excess of ethanol with overnight incubation at −20° C., followed by centrifugation and storage at −20° C. until further purification.

Protein Purification:

The acid cleaved binding site was separated from remaining intact fused protein species by chromatography on DEAE cellulose. The precipitate obtained from the cleavage mixture was redissolved in 6 M guanidine-HCl +0.2 M Tris-HCl, pH 8.2,+0.1 M 2-mercaptoethanol and dialyzed exhaustively against 6 M urea +2.5 mM Tris-HCl, pH 7.5,+1 mM EDTA. 2-Mercaptoethanol was added to a final concentration of 0.1 M, the solution was incubated for 2 hrs at room temperature and loaded onto a 2.5 X 45 cm column of DEAE cellulose (Whatman DE 52), equilibrated with 6 M urea +2.5 mM Tris-HCl +1 mM EDTA, pH 7.5. The intact fusion protein bound weakly to the DE 52 column such that its elution was retarded relative to that of the binding protein. The first protein fractions which eluted from the column after loading and washing with urea buffer contained BABS protein devoid of intact fusion protein. Later fractions contaminated with some fused protein were pooled, rechromatographed on DE 52, and recovered single chain binding protein combined with other purified protein into a single pool.

Refolding:

The 26–10 binding site mimic was refolded as follows: the DE 52 pool, disposed in 6 M urea +2.5 mM Tris-HCl +1 mM EDTA, was adjusted to pH 8 and reduced with 0.1 M 2-mercaptoethanol at 37° C. for 90 min. This was diluted at least 100-fold with 0.01 M sodium acetate, pH 5.5, to a concentration below 10 μg/ml and dialyzed at 4° C. for 2 days against acetate buffer.

Affinity Chromatography:

Purification of active binding protein by affinity chromatography at 4° C. on a ouabain-amine-Sepharose column was performed. The dilute solution of refolded protein was loaded directly onto a pair of tandem columns, each containing 3 ml of resin equilibrated with the 0.01 M acetate buffer, pH 5.5. The columns were washed individually with an excess of the acetate buffer, and then by sequential additions of 5 ml each of 1 M NaCl, 20 mM ouabain, and 3 M potassium thiocyanate dissolved in the acetate buffer, interspersed with acetate buffer washes. Since digoxin binding activity was still present in the eluate, the eluate was pooled and concentrated 20-fold by ultrafiltration (PM 10 membrane, 200 ml concentrator; Amicon), reapplied to the affinity columns, and eluted as described. Fractions with significant absorbance at 280 nm were pooled and dialyzed against PBSA or the above acetate buffer. The amounts of protein in the DE 52 and ouabain-Sepharose pools were quantitated by amino acid analysis following dialysis against 0.01 M acetate buffer. The results are shown below in Table 1.

TABLE 1

Estimated Yields of BABS Protein During Purification

| Step | Wet wt. Per 1 | mg protein | Cleavage yield (%) prior step | Yield relative to fusion protein |
|---|---|---|---|---|
| Cell paste | 12.0 g | 1440.0 mg[a] | | |
| Fusion protein Granules | 2.3 g | 480.0 mg[a, b] | 100.0% | 100.0% |
| Acid Cleavage/ DE 52 pool | | 144.0 mg | 38.0[c] | 38.0[e] |
| Ouabain-Sepharose pool | | 18.1 mg | 12.6[d] | 4.7[e] |

[a]Determined by Lowry protein analysis
[b]Determined by absorbance measurements
[c]Determined by amino acid analysis
[d]Calculated from the amount of BABS protein specifically eluted from ouabain-Sepharose relative to that applied to the resin; values were determined by amino acid analysis
[e]Percentage yield calculated on a molar basis Sequence Analysis of Gene and Protein:

The complete gene was sequenced in both directions using the dideoxy method of Sanger which confirmed the gene was correctly assembled. The protein sequence was also verified by protein sequencing. Automated Edman degradation was conducted on intact protein (residues 1–40), as well as on two major CNBr fragments (residues 108–129 and 140–159) with a Model 470A gas phase sequencer equipped with a Model 120A on-line phenylthiohydantoin-amino acid analyzer (Applied Biosystems, Foster City, Calif.). Homogeneous binding protein fractionated by SDS-PAGE and eluted from gel strips with water, was treated with a 20,000-fold excess of CNBr, in 1% trifluoroacetic acid-acetonitrile (1:1), for 12 hrs at 25° (in the dark). The resulting fragments were separated by SDS-PAGE and transferred electrophoretically onto an Immobilon membrane (Millipore, Bedford, Mass.), from which stained bands were cut out and sequenced.

Characterization of Binding Properties

Specificities of anti-digoxin 26–10 Fab and the BABS were assessed is parallel by radioimmunoassay. Wells of microtiter plates were coated with affinity-purified goat anti-murine Fab fragment (ICN ImmunoBiologicals, Lisle, Ill.) at 10 mg/ml in PBSA overnight at 4° C. After the plates were washed and blocked with 1% horse serum in PBSA, solutions (50 ml) containing 26–10 Fab or the BABS in either PBSA or 0.01 M sodium acetate at pH 5.5 were added to the wells and incubated 2–3 hrs at room temperature. After unbound antibody fragment was washed from the wells, 25 ml of a series of concentrations of cardiac glycosides ($10^{-4}$ to $10^{-11}$ M in PBSA) were added. The cardiac glycosides tested included digoxin, digitoxin, digoxigenin, digitoxigenin, gitoxin, ouabain, and acetyl strophanthidin. The BABS was found to bind with oleandrin in a separate experiment described below. After the addition of $^{125}$I-digoxin (25 ml, 50,000 cpm; Cambridge Diagnostics, Billerica, Mass.) to each well, the plates were incubated overnight at 4° C., washed and counted. The relative affinities for each digoxin analog were calculated by dividing the concentration of each analogue at 50% inhibition by the concentration of digoxin (or digoxigenin) that gave 50% inhibition. There is a displacement of inhibition curves for the BABS to lower glycoside concentrations than observed for 26–10 Fab, because less active BABS than 26–10 Fab was bound to the plate. When 0.25 M urea was added to the BABS in 0.01 M sodium acetate, pH 5.5, more active sFv was bound to the goat anti-murine Fab coating on the plate. This caused the BABS inhibition curves to shift toward higher glycoside concentrations, closer to the position of those for 26–10 Fab, although maintaining the relative positions of curves for sFv obtained in acetate buffer alone. The results, expressed as normalized concentration of inhibitor giving 50% inhibition of $^{125}$I-digoxin binding, are shown in Table 2.

TABLE 2

| 26-10 Antibody Species | Normalizing Glycoside | D | DG | DO | DOG | A-S | G | O |
|---|---|---|---|---|---|---|---|---|
| Fab | Digoxin | 1.0 | 1.2 | 0.9 | 1.0 | 1.3 | 9.6 | 15 |
| | Digoxigenin | 0.9 | 1.0 | 0.8 | 0.9 | 1.1 | 8.1 | 13 |
| BABS | Digoxin | 1.0 | 7.3 | 2.0 | 2.6 | 5.9 | 62 | 150 |
| | Digoxigenin | 0.1 | 1.0 | 0.3 | 0.4 | 0.8 | 8.5 | 21 |

D = Digoxin
DG = Digoxigenin
DO = Digitoxin
DOG = Digitoxigenin
A-S = Acetyl Strophanthidin
G = Gitoxin
O = Ouabain Association constants were measured by equilibrium binding studies in 0.01M potassium acetate buffer (pH 5.5) containing 0.25M urea. In immunoprecipitation experiments, 100 ml of $^3$H-digoxin (New England Nuclear, Billerica, Mass.) at a series of concentrations ($10^{-7}$ M to $10^{-11}$ M) were added to 100 ml of 26–10 Fab or the BABS at a fixed concentration. After 2–3 hrs of incubation at room temperature, the protein was precipitated by the addition of 100 ml goat antiserum to murine Fab fragment (ICN ImmunoBiologicals), 50 ml of the IgG fraction of rabbit anti-goat IgG (ICN ImmunoBiologicals), and 50 ml of a 10% suspension of protein A-Sepharose (Sigma). Following 2 hrs at 4° C., bound and free antigen were separated by vacuum filtration on glass fiber filters (Vacuum Filtration Manifold, Millipore, Bedford, Mass.). Filter disks were then counted in 5 ml of scintillation fluid with a Model 1500 Tri-Carb Liquid Scintillation Analyzer (Packard, Sterling, Va.). The association constants, $K_o$, were calculated from Scatchard analyses of the untransformed radioligand binding data using LIGAND, a non-linear curve fitting program based on mass action. $K_o$s were also calculated by Sips plots and binding isotherms shown in FIG. 10 for the BABS and 11 for the Fab. For binding isotherms, data are plotted as the concentration of digoxin bound versus the log of the unbound digoxin concentration, and the dissociation constant is estimated from the ligand concentration at 50% saturation. These binding data are also plotted in linear form as Sips plots (inset), having the same abscissa as the binding isotherm but with the ordinate representing log $r/(n-r)$, defined below. The average intrinsic association constant ($K_o$) was calculated from the modified Sips equation (39), log $(r/n-r)=a \log C - a \log K_o$, where r equals moles of digoxin bound per mole of antibody at an unbound digoxin concentration equal to C; n is the number of moles of digoxin bound at saturation of the antibody binding site, and a is an index of heterogeneity which describes the distribution of association constants about the average intrinsic association constant $K_o$. Least squares linear regression analysis of the data indicated correlation coefficients for the lines obtained were 0.96 for the BABS and 0.99 for 26-10 Fab. A summary of the calculated association constants are shown below in Table 3.

TABLE 3

| Method of Data Analysis | Association Constant, $K_o$ | |
|---|---|---|
| | $K_o$ (BABS), $M^{-1}$ | $K_o$ (Fab), $M^{-1}$ |
| Scatchard plot | $(3.2 \pm 0.9) \times 10^7$ | $(1.9 \pm 0.2) \times 10^8$ |
| Sips plot | $2.6 \times 10^7$ | $1.8 \times 10^8$ |
| Binding isotherm | $5.2 \times 10^7$ | $3.3 \times 10^8$ |

Collectively these data demonstrate that the BABS has an affinity and specificity similar to its 26-10 parent molecule, but has a molecular weight on the order of ten times lower.

Synthesis of a Fusion Protein

A nucleic acid sequence encoding the single chain binding site described above was fused with a sequence encoding the FB fragment of protein A as a leader. As a spacer, the native amino acids comprising the last 11 amino acids of the FB fragment bonded to an Asp-Pro dilute acid cleavage site was employed. The FB binding domain of the FB consists of the immediately preceding 43 amino acids which assume a helical configuration (see FIG. 7B).

The gene fragments are synthesized using a Biosearch DNA Model 8600 Synthesizer as described above. Synthetic oligonucleotides are cloned according to established protocol described above using the pUC8 vector transfected into *E. coli.* The completed fused gene set forth in FIG. 6 is then expressed in *E. coli.*

After sonication, inclusion bodies were collected by centrifugation, and dissolved in 6 M guanidine hydrochloride (GuHCl), 0.2 M Tris, and 0.1 M 2-mercaptoethanol (BME), pH 8.2. The protein was denatured and reduced in the solvent overnight at room temperature. Size exclusion chromatography was used to purify fusion protein from the inclusion bodies. A Sepharose 4B column (1.5×80 cm) was run in a solvent of 6 M GuHCl and 0.01 M NaOAc, pH 4.75. The protein solution was applied to the column at room temperature in 0.5-1.0 ml amounts. Fractions were collected and precipitated with cold ethanol. These were run on SDS gels, and fractions rich in the recombinant protein (approximately 34,000 D) were pooled. This offers a simple first step for cleaning up inclusion body preparations without suffering significant proteolytic degradation. An alternative purification (procedure involves dialysis of solubilized protein into 2.5mM Tris, 1 mM EDTA, and 5mM DTT, pH8. Passage through a DEAE cellulose column (DE52) equilibrated with this buffer yields fusion protein suitable for refolding by procedure 2.

For refolding, the protein was dialyzed against 100 ml of the same GuHCl-Tris-BME solution, and dialysate was diluted 11-fold over two days to 0.55 M GuHCl, 0.01 M Tris, and 0.01 M BME. The dialysis sacks were then transferred to 0.01 M NaCl, and the protein was dialyzed exhaustively before being assayed by RIA's for binding of $^{125}$I-labelled digoxin. The refolding procedure can be simplified by making a rapid dilution with water to reduce the GuHCl concentration to 1.1 M, and then dialyzing against phosphate buffered saline (0.15 M NaCl, 0.05 M potassium phosphate, pH 7, containing 0.03% $NaN_3$), so that it is free of any GuHCl within 12 hours. Product of both types of preparation showed digoxin binding activity very similar to the parent antibody, as indicated in FIG. 8.

Procedure 2 involves dilution of DE52 pool into 3M urea, lmM oxidized glutathione, 0.lmM reduced glutathione, pH8, where it resides for 15 hours at room temperature, followed by dialysis into 50mM sodium phosphate, pH7. Subsequently, the active fusion protein is isolated by oubain-Sepharose chromatography as described above.

Demonstration of Binding Abilities

Properties of the binding site were probed by a modification of an assay developed by Mudgett-Hunter et al. (J. Immunol. (1982) 129:1165-1172; Molec. Immunol. (1985) 22:477-488), so that it could be run on microtiter plates as a solid phase sandwich assay. Binding data were collected using goat anti-murine Fab antisera (gAmFab) as the primary antibody that initially coats the wells of the plate. These are polyclonal antisera which recognize epitopes that appear to reside mostly on framework regions. The samples of interest are next added to the coated wells and incubated with the gAmFab, which binds species that exhibit appropriate antigenic sites. After washing away unbound protein, the wells are exposed to $^{125}$I-labelled (radioiodinated) digoxin conjugates, either as $^{125}$I-dig-BSA or $^{125}$I-dig-lysine.

The data are plotted in FIG. 8, which shows the results of a dilution curve experiment in which the parent 26-10 antibody was included as a control. The sites were probed with $^{125}$I-dig-BSA as described above, with a series of dilutions prepared from initial stock solutions, including both the slowly refolded (1) and fast diluted/quickly refolded (2) single chain proteins. The parallelism between all three dilution curves indicates that gAmFab binding regions on the BABS molecule are essentially the same as on the Fv of authentic 26-10 antibody, i.e., the surface epitopes appear to be the same for both proteins.

The sensitivity of these assays is such that binding affinity of the Fv for digoxin must be at least $10^6$. Experimental data on digoxin binding of protein prepared by procedure 2 yielded binding constants of about $2\times10^9$ $M^{-1}$ The parent 26-10 antibody has an affinity of $5.4\times10^9 M^{-1}$ Inhibition assays also indicate the binding of $^{125}$I-dig-lysine antisera (gAmFab) as the primary antibody that initially coats the wells of the plate. These are polyclonal antisera which recognize epitopes that appear to reside mostly on framework regions. The samples of interest are next added to the coated wells and incubated with the gAmFab, which binds species that exhibit appropriate antigenic sites. After washing away unbound protein, the wells are exposed to $^{125}$I-labelled (radioiodinated) digoxin conjugates, either as $^{125}$I-dig-BSA or $^{125}$I-dig-lysine.

The data are plotted in FIG. 8, which shows the results of a dilution curve experiment in which the parent 26-10 antibody was included as a control. The sites were probed with $^{125}$I-dig-BSA as described above, with a series of dilutions prepared from initial stock solutions, including both the slowly refolded (1) and fast diluted/quickly refolded (2) single chain proteins. The parallelism between all three dilution curves indicates that gAmFab binding regions on the BABS molecule are essentially the same as on the Fv of authentic 26-10 antibody, i.e., the surface epitopes appear to be the same for both proteins.

The sensitivity of these assays is such that binding affinity of the Fv for digoxin must be at least $10^6$. Experimental data on digoxin binding of protein prepared by procedure 2 yielded binding constants of about $2\times10^9$ $M^{-1}$ The parent 26-10 antibody has an affinity of $5.4\times10^9$ $M^{-1}$. Inhibition assays also indicate the binding of $^{125}$I-dig-lysine can be inhibited by unlabelled digoxin, digoxigenin, digitoxin, digitoxigenin, gitoxin, acetyl strophanthidin, oleandrin, and ouabain in a way largely parallel to the parent 26-10 Fab. This indicates that the specificity of the biosynthetic protein is substantially identical to the original monoclonal.

A hollow fiber device was constructed using 100×17.8 cm PAN fibers, produced by Sepracor, Inc., Marlborough, Mass. Each PAN fiber is a tubular membrane having a wall thickness of 50 μm and an internal diameter of 205 μm. Thus, this device contains a geometric surface area of 115 $cm^2$ of PAN fiber. The associated fluid handling equipment comprised two peristaltic pumps, one for the shell loop and one for the luman loop, a pressure gauge on the shell loop for determining the pressure drop from the shell side to the lumen side, and a throttling valve for creating a positive pressure on the shell side.

The device was first washed with 1 L of water. This washing involved convecting water through the lumen, through the shell, and through the PAN fibers from shell-side to lumen.

Following the washing procedure, the liquid membrane was put in place. A buffer solution of the same composition as that in which the FB-sFv protein was dissolved (50 mM sodium chloride) was pumped through the fibers, from the shell-side to the lumen. Approximately 100 mls of buffer solution were convected through the fibers. Both the lumen and shell were then drained of bulk aqueous solution, and 1-octanol previously saturated with the same buffer solution was introduced into both the shell and lumen fluid loops. After establishing uninterrupted convection of 1-octanol through these loops, the throttling valve was closed until a shell-to-lumen pressure drop of 10 psi was created across the fibers. The octanol in both the shell and lumen loops were fed from separate reservoirs, both containing 100 mls of 1-octanol previously saturated with the same buffer used as the supported liquid membrane.

The volumes of both reservoirs were carefully monitored under these conditions, and were observed not to change over 20 hours. Thus, the supported liquid membrane did not permit octanol from the shell fluid loop to pass through the fibers to the lumen fluid loop, despite the 10 psi pressure differential.

Oleandrin is a cardiac glycoside having a molecular weight of 576, and an organic to aqueous partition coefficient between 1-octanol and water of 338 (Cohnen et al, Drug Res. 28 (II), Heft 12, 1978). This translates to an aqueous to organic coeffient S of about 0.003. The glycoside was dissolved to a final concentration of 2.0 mgs/ml (3.5 mM) in 500 mls of 1-octanol previously saturated with buffer. This reservoir was then placed in the shell fluid loop. A reservoir containing 50 ml of buffer saturated 1-octanol, containing no oleandrin, was placed in the lumen fluid loop, and circulation of these reservoirs through their respective fluid loops commenced. The pressure differential of 10 psi was maintained across the supported liquid membrane. The volumes of the reservoirs were noted, and again observed not to change over a 20 hour period. During this period, successive 1 ml samples of the lumen reservoir were taken. In order not to disturb the volume of the lumen reservoir, the octanol taken in each sample was replaced with 1 ml of buffer saturated octanol after drawing each sample. The quantity of oleandrin contained in each lumen reservoir sample was determined by HPLC. Samples taken before 6 hours had elapsed did not demonstrate detectable quantities of oleandrin. Samples taken at 19 and 20 hours showed oleandrin concentrations in the lumen reservoir of 0.05 mg/ml and 0.04 mg/ml respectively.

The fluid loops were then drained. 100 mls of buffer containing 10.0 mgs of FB-sFv 26-10 produced as disclosed above were then slowly ultrafiltered from the shell loop at a pressure of 10 psi. This filtration proved extremely slow, and the process was allowed to proceed for 24 hours. After this time, no bulk fluid, either aqueous or organic, was present in either loop. The aqueous ultrafiltrate was observed at 280nm, and found to have an absorbance of 0.04. Since an optical density of 1.0 at 280 nm indicates a protein concentration of 1.0 mg/ml, the filtrate contained 4.0 mgs protein. 6.0 mgs of FB-sFv 26-10 were therefore assumed to be contained in the supported liquid membrane.

Octanol saturated with buffer, but not containing oleandrin, was then convected through each loop, with the 10 psi pressure differential across the supported liquid membrane. Once uninterrupted convection through each loop was established, the shell loop reservoir was replaced with a reservoir containing 500 mls of octanol saturated with buffer, and containing 2.0 mg/ml oleandrin. The lumen reservoir was replaced with a reservoir containing 50 mls of buffer saturated octanol, containing no oleandrin. Over a 24 hour period, no convective flow of octanol through the supported liquid membrane occurred.

During this period, successive 1 ml samples of the lumen reservoir were taken. In order not to disturb the volume of the lumen reservoir, the octanol taken in each sample was replaced with 1 ml of buffer saturated octanol after drawing each sample. The quantity of oleandrin contained in each lumen reservoir sample was determined by HPLC. The data for the foregoing experiments is summarized in the Table below.

| time (hrs) | oleandrin concentration (mg/ml) |
|---|---|
| No Binding Protein in Membrane | |
| 0 | 0 |
| 19.0 | 0.050 |
| 20.0 | 0.040 |
| 6.0 mgs. Binding Protein in Membrane | |
| 0 | 0 |
| 0.5 | 0.016 |
| 1.0 | 0.025 |
| 2.0 | 0.047 |
| 3.0 | 0.067 |
| 4.0 | 0.090 |
| 6.0 | 0.119 |
| 7.0 | 0.134 |
| 7.5 | 0.140 |
| 23.0 | 0.335 |
| 24.0 | 0.350 |

These data, together with the data obtained when the supported liquid membrane did not contain any protein, is plotted on the attached FIG. 12. Using a polynomials curve-fitting procedure, the first order polynomial (slope) of the curve of the change in oleandrin concentration in the absence of the binding protein is 0.0023 mg/ml/hr. The first order polynomial for the change in concentration of oleandrin in the presence of the binding protein is 0.0215 mg/ml/hr, corresponding to the rate of change of the oleandrin concentration in the receiving reservoir at time zero. These numbers represent the flux of oleandrin through the supported liquid membrane. In the presence of the 26-10 protein, an initial increase of oleandrin flux of (0.0215/0.0023), or 9.3-fold, was observed. Over the 24 hour time period of the experiment with facilitated transport, a turnover number of the protein molecules may be calculated. Assuming a molecular weight of 32,000 for the binding protein molecule, the turnover number is 140.

The initial flux of oleandrin across the BABS-containing membrane was $4.9\times10^{-12}$ gmole/sec-cm$^2$ and the average flux during the 24-hour experiment was $2.9\times10^{-12}$ gmole/sec-cm$^2$ These initial and average fluxes correspond to permeabilities (based on organic-phase concentration difference driving forces) of $3.4\times10^{-6}$ and $8.4-10^{7}$ cm/sec, respectively. The intial facilitation factor was 8.3, and the corresponding 24-hour average value was 4.5.

Thus, as expected, the FB-Fv 26-10 binds oleandrin in a manner quantitatively similar to its parent monoclonal antibody and may be used as a binding protein to facilitate transport in an immobilized liquid membrane of oleandrin.

EXAMPLE 2

In this example, a membrane process is described for the separation of stereoisomers of naproxen esters. The process is based on the use of an enantioselective biosynthetic antibody binding site (BABS) protein that serves as the carrier in a facilitated transport process conducted in an immobilized liquid membrane.

Naproxen is a chiral pharmaceutical of considerable commercial importance. It is the S(+) isomer of 2-(6-methoxy-2-naphthyl) propionic acid. It is widely used to control the symptoms of arthritis. The S(+) enantiomer of naproxen is known to be 28 times more potent as an anti-inflammatory than is its R(−) counterpart.

Naproxen may be resolved in a multistep process that involves forming a racemic mixture of the ester derivative, separating the ester stereoisomers in a facilitated-transport process based on a BABS protein as the carrier, and recovering the desired S(+) acid through chemical hydrolysis of the S(+) ester. Only the separation step is described here.

Although the naproxen acid itself is water-soluble to an extent approaching perhaps 0.1 M at neutral pH, the esters formed by reacting naproxen with simple alcohols are solids that are only sparingly soluble in water. For instance, the solubility in water of the racemic ethyl ester of naproxen (molecular weight 258) is not accurately known but probably does not exceed 0.1 mM; for present purposes, we assume a racemate solubility of only 0.01 mM or 10 $\mu$M. Because the ester is soluble in organic solvents such as toluene to the extent of moles per liter, the aqueous-to-organic partition or solubility coefficient as defined above is about $10^{-5}$. Thus, the naproxen ester resolution process of the present example is based on a water-soluble BABS protein contained as an aqueous phase in the pores of a hydrophilic support membrane. The feed stream to the membrane separator consists of a 1 M racemic solution of the naproxen ethyl ester dissolved in toluene.

Monoclonal antibodies to the chiral center of naproxen (carbon 2 of the propionic acid moiety) are raised against naproxen employing techniques well known to those skilled in the art. For example naproxen may be conjugated at the 6 position of its napthalene ring to hemocyanin. Procedures for generating murine hybridoma fusions are current versions of the Kohler-Milstein procedure. Monoclonal antibodies are screened as follows: (1) all antibodies cross-reactive with hemocyanin alone are excluded, as are antibodies that bind the naproxin-hemocyanin conjugate but not free naproxen (representing so-called link antibodies); (2) remaining clones are tested for reactivity with free naproxen in ELISA or RIA assays, and positive clones are screened further; (3) remaining hybridoma clones are tested for reactivity against (+) naproxen and against (−) naproxen; (4) only those cell lines secreting antibodies that react strictly against (+) naproxen are considered as potential candidates for the basis of BABS protein construction; (5) affinities and kinetic parameters are determined for the candidate molecules, and a monoclonal antibody with appropriate values is chosen for application. Alternatively, single domain binding sites with lowered affinity can be generated by protein chemistry or recombinant DNA methods from candidates surviving step (5) of the screening process, and these species can be rescreened by steps (3), (4), and (5) to arrive at a group of lower affinity BABS candidates. The cDNA cloning and BABS construction of the molecule of choice follow the procedures described above.

The support membrane consists of an asymmetric, ultrafiltration-type hollow-fiber membrane fabricated via conventional solvent phase inversion techniques and encapsulated via a solvent-resistant epoxy into a conventional hollow-fiber module containing large numbers of fibers. Hollow-fiber membranes and modules containing from 0.75 to 8.5 square meters of such fiber are manufactured by Sepracor Inc., Marlborough, Mass. from a hydrophilic polyacrylonitrile (PAN)-based copolymer containing several weight percent of a methyl acrylate component. Similar hydrophilic, PAN-copolymer-based membranes are made for hemofiltration applications by, for example, Asahi Medical Company; they are packaged in 1.0 square meter modules (e.g., Asahi's Model PAN 150 hemofilter).

The liquid membrane support membrane is further characterized by a porosity $\epsilon$ of 80% and a tortuosity $\tau$ of 1.6. The inner and outer diameters of the fiber are 200 and 280 microns, respectively, corresponding to a hollow-fiber membrane wall thickness of 40 microns.

The first step in the liquid membrane preparation involves preparing an appropriately buffered aqueous solution of the BABS protein. Generally speaking, it will be desirable to use as concentrated a solution of the BABS protein as possible, at least insofar as its viscosity is not excessive. The BABS protein employed in this example is designed as explained above to have a water solubility of about 10 mg/mL, corresponding to a molar water solubility of approximately 0.0005 M. The viscosity of this BABS protein solution at ambient temperature is only slightly greater than 1 centipoise, illustrating that the viscosity-associated limit on protein concentration has not been approached.

Effective diffusivities of the naproxen ethyl ester $D_A$ and of the BABS/naproxen ester complex ($D_{CA}$) may be estimated from equation (4) above using predictions of the free-solution diffusivities of these species (estimated at infinite dilution in water at about $7.5\times10^{-6}$ and $1.0\times10^{-6}$ cm²/sec, respectively, for the solute and the complex) and using values provided above for the support membrane porosity and tortuosity. In this manner, effective liquid membrane diffusivities of free solute and protein/solute complex of $3.8\times10^{-6}$ and $5.0\times10^{-7}$ cm²/sec are obtained, respectively.

The BABS protein is selected as detailed above so as to possess a nearly optimal affinity for S(+) naproxen ethyl ester binding, and essentially complete enantioselectivity for binding the S(+) in preference to the R(−) isomer. It has been further explained above that the optimum binding constant K depends, in general, on aqueous-phase target solute concentrations at the feed stream and product stream membrane interfaces $C_{A1}$ and $C_{A2}$, which in turn are related to organic phase feed stream and product stream concentrations through the partition or solubility coefficient.

In the present instance, the concentration $C_{A1}$ at equilibrium with the initial or inlet concentration of the S(+) naproxen ester in the toluene feed solution is about 0.005 mM, or about one-half of the water solubility of the racemate (0.01 mM). Depletion of the extracted S(+) isomer as it is removed from the feed during the resolution process further lowers the average effective concentration $C_{A1}$ to about one-half of the initial or inlet value, or to about 0.0025 mM. A stream of toluene is supplied to the opposite side of the membrane in order to dilute and remove from the separator the S(+)-naproxen ester that permeates the membrane. The flowrate of this product stream is adjusted to be several times greater than that of the racemic feed stream in order to provide sufficient driving force for the facilitated transport process. Specifically, the average product-side aqueous-phase concentration $C_{A2}$ is maintained at about 10% of that at the interface of the membrane with the feed stream, or 0.25 μM.

Equation (12) above predicts that the optimum value of the equilibrium binding will be given by the reciprocal of the geometric mean of these concentrations $C_{A1}$ and $C_{A2}$. In the present instance, this corresponds to an optimum affinity of about $1.26\times10^{6}$ liters/mole. The BABS protein is also selected to have favorable solute binding and release kinetics, consistent with having small Damkohler numbers as calculated above. In accordance with equation (6), the facilitation factor F obtained with this BABS protein as solute carrier is approximately 15.

The significance of this facilitation factor may be appreciated further with the aid of equation (2), which indicates that 15 times more S(+) ester permeates across the liquid membrane in the form of its complex with BABS than crosses the liquid membrane by passive diffusion. The passive diffusion fluxes of the S(+) and R(−) enantiomers are equal, with the result that the S(+) naproxen ester stereoisomer permeates across the membrane 16 times more rapidly (as both the free solute and in the form of its complex with protein) than does the corresponding R(−) ester by passive diffusion alone. Accordingly, the enantiomeric excess of the S(+) naproxen ester product is about (16−1) / (16+1) or 88%.

The S(+) naproxen ester flux of about $3.4\times10^{-11}$ mole/sec-cm² is consistent with that predicted with the aid of equations (2) and (3).

The invention may be embodied in other specific forms, and accordingly, other embodiments are within the following claims.

What is claimed is:

1. Apparatus for separating a solute from a mixture, the apparatus comprising:
- a first membrane;
- a hydrophilic liquid phase immobilized within said first membrane;
- means for passing a hydrophobic feed solution into reactive contact with a first interface at a first surface of said first membrane, said hydrophobic feed solution comprising a mixture including a desired solute in a solvent substantially immiscible with said membrane immobilized hydrophilic liquid phase;
- a binding protein dissolved in and substantially confined within said hydrophilic liquid phase within said membrane, substantially insoluble in said hydrophobic feed solution, and having a binding specificity for said solute in preference to other solutes in said hydrophobic solution, for immunochemically binding said solute at said interface and
- means for passing a product stream into reactive contact with said hydrophilic liquid phase immobilized within the membrane at a second interface opposite said first interface of said first membrane
- thereby to produce a concentration gradient of a complex of the solute and binding protein across said first membrane sufficient to transport said complex from said first interface to said second interface by diffusion, and
- to produce a concentration gradient of said binding protein across said first membrane sufficient to transport said binding protein from said second interface to said first interface by diffusion, said binding protein thereby serving to facilitate preferential transport of said solute across said membrane from said feed solution to said product stream.

2. Apparatus for separating a solute from a mixture, the apparatus comprising:
- first membrane;
- a second membrane;
- a hydrophilic liquid phase disposed between said first and second membranes;
- means for passing a hydrophobic feed solution into reactive contact with said hydrophilic liquid phase at a first surface of said first membrane, said hydrophobic feed solution comprising a mixture including a desired solute in a solvent substantially immiscible with said hydrophilic liquid phase;
- means for passing a product stream into reactive contact with said hydrophilic liquid phase at a second surface at said second membrane;
- a binding protein dissolved and substantially confined within said hydrophilic liquid phase, substantially insoluble in said feed solution and said product solution, and having a binding specificity for said solute in preference to other solutes in said feed solution, for immunochemically binding and extracting said solute from said feed solution at said first membrane, and for releasing solute into said product stream at said second membrane; and
- means for convectively circulating said hydrophilic liquid phase between said first and second membranes, thereby to transport a complex of the solute and binding protein through the hydrophilic liquid phase from the first membrane to the second membrane and to transport binding protein through the hydrophilic liquid phase from said second membrane to said first membrane and thereby to effect selective net transport of said solute from said feed solution to said product stream.

3. The apparatus of claim 1 or 2 wherein said binding protein comprises a first domain defining a binding site comprising at least 3 CDR regions held in binding conformation by FR regions.

4. The apparatus of claim 3 wherein said binding protein further comprises:

a second domain for imparting to said binding protein solubility in said hydrophilic liquid phase.

5. The apparatus of claim 1 or 2 wherein said binding protein has a binding specificity for one member of a pair of optically active proteins.

6. The apparatus of claim 1 or 2 wherein said binding protein has an affinity for said solute between $10^3$ and $10^9\ M^{-1}$.

7. A process for separating a solute from a mixture, the process comprising the steps of a) immobilizing a hydrophilic liquid phase within a porous membrane, said hydrophilic liquid phase comprising a dissolved binding protein having a binding specificity for said solute;

b) passing a hydrophobic feed solution into reactive contact with said hydrophilic liquid phase at a first interface at said membrane to promote immunochemical binding between said solute in said hydrophobic feed solution and said binding protein, said hydrophobic feed solution comprising a mixture including said solute in a solvent substantially immiscible with said hydrophilic liquid phase;

c) passing a product stream into reactive contact with said hydrophilic liquid phase at a second interface at said membrane to dissolve said solute within said product stream, thereby to promote dissociation of said binding protein solute complex;

produce a concentration gradient of said complex within and across said membrane sufficient to transport said complex from said first interface to said second interface by diffusion and produce a concentration gradient of said binding protein across said membrane sufficient to transport said binding protein from said second interface to said first interface by diffusion.

8. A process for separating a solute from a mixture, the process comprising the steps of a) maintaining between and in contact with at least first and second membranes a hydrophilic liquid phase comprising a dissolved binding protein having a binding specificity for said solute;

b) passing a hydrophobic feed solution into reactive contact with a first interface at one of said membranes to promote formation of an immunochemically bonded complex comprising said solute and said binding protein at said first interface, said hydrophobic feed solution comprising a mixture including said solute in a solvent substantially immiscible with said hydrophilic liquid phase;

c) passing a product stream into reactive contact with said hydrophilic liquid phase at a second interface at said second membrane to extract said solute into said product stream and to promote dissociation of said solute binding protein complex; and d) convectively circulating said hydrophilic liquid phase between said first and second interfaces to effect selective net transport of said solute from said hydrophobic feed solution to said product stream.

9. The process of claim 7 or 8 wherein said binding protein comprises a first domain defining a binding site comprising at least three CDR regions held in binding confirmation by FR regions.

10. The process of claim 9 wherein said binding protein further comprises a second domain for imparting to said binding protein solubility in said liquid phase.

11. The process of claim 7 or 8 wherein said binding protein as a binding specificity for one member of a pair of optically active compounds.

12. The process of claim 7 or 9 wherein said binding protein has an affinity for said preselected solute between $10^3$ and $10^9\ M^{-1}$.

* * * * *

UNITED STATES PATENT AND TRADEMARK OFFICE

CERTIFICATE OF CORRECTION

PATENT NO. : 5,167,824

DATED : December 1, 1992

INVENTOR(S) : Charles Cohen et al.

It is certified that error appears in the above-identified patent and that said Letters Patent is hereby corrected as shown below:

In claim 2, line 3, (. column 36, line 38), insert --a-- before "first membrane".

In claim 5, last line ( column 37, line 14), replace "proteins" with --compounds--.

In claim 9, lines 4-5 ( column 38, lines 31-32), replace "confirmation" with --conformation--.

In claim 11, second line ( column 38, line 38), replace "as" with --has--.

In claim 12, first line ( column 38, line 40), replace "9" with --8--.

Signed and Sealed this

Ninth Day of November, 1993

Attest:

BRUCE LEHMAN

*Attesting Officer*

*Commissioner of Patents and Trademarks*